United States Patent
Cote et al.

(10) Patent No.: US 11,589,588 B2
(45) Date of Patent: Feb. 28, 2023

(54) METHODS OF IDENTIFICATION AND USE OF NEMATICIDE COMPOUNDS

(71) Applicant: UNIVERSITY OF NEW HAMPSHIRE, Durham, NH (US)

(72) Inventors: Richard H. Cote, Lee, NH (US); Karyn B. Cahill, Durham, NH (US); Kevin D. Schuster, Rochester, NY (US)

(73) Assignee: University of New Hampshire, Durham, NH (US)

( * ) Notice: Subject to any disclaimer, the term of this patent is extended or adjusted under 35 U.S.C. 154(b) by 527 days.

(21) Appl. No.: 16/744,307

(22) Filed: Jan. 16, 2020

(65) Prior Publication Data

US 2020/0138032 A1 May 7, 2020

Related U.S. Application Data

(62) Division of application No. 14/776,827, filed as application No. PCT/US2014/029910 on Mar. 15, 2014, now Pat. No. 10,561,144.

(60) Provisional application No. 61/793,374, filed on Mar. 15, 2013.

(51) Int. Cl.
| | |
|---|---|
| *A01N 43/90* | (2006.01) |
| *A01N 43/36* | (2006.01) |
| *A01N 43/42* | (2006.01) |
| *A01N 43/713* | (2006.01) |
| *C12Q 1/04* | (2006.01) |
| *G01N 33/50* | (2006.01) |
| *A01N 43/40* | (2006.01) |
| *C12Q 1/44* | (2006.01) |

(52) U.S. Cl.
CPC ............ *A01N 43/90* (2013.01); *A01N 43/36* (2013.01); *A01N 43/40* (2013.01); *A01N 43/42* (2013.01); *A01N 43/713* (2013.01); *C12Q 1/04* (2013.01); *C12Q 1/44* (2013.01); *G01N 33/5017* (2013.01); *G01N 33/5085* (2013.01); *C12N 2501/01* (2013.01); *C12Q 2527/127* (2013.01); *G01N 2500/04* (2013.01)

(58) Field of Classification Search
None
See application file for complete search history.

(56) References Cited

U.S. PATENT DOCUMENTS

| | | | | |
|---|---|---|---|---|
| 4,902,690 A | ‡ | 2/1990 | Nathanson | A01N 43/90 |
| 8,067,671 B2 | ‡ | 11/2011 | Boukharov | C07K 14/4354 |
| | | | | 800/28 |
| 8,347,551 B2 | ‡ | 1/2013 | Van Der Drift | A01N 37/40 |
| | | | | 47/57 |
| 2008/0038383 A1 | ‡ | 2/2008 | Bessette | A01N 31/04 |
| | | | | 424/74 |
| 2011/0200571 A1 | ‡ | 8/2011 | Bell | A01C 1/08 |
| | | | | 424/93 |

FOREIGN PATENT DOCUMENTS

| | | | | |
|---|---|---|---|---|
| WO | 2001/40500 A1 | 6/2001 | | |
| WO | WO-200140500 A1 ‡ | 6/2001 | | |
| WO | 2006060333 A2 | 6/2006 | | |
| WO | WO-2006060333 A2 ‡ | 6/2006 | ............ | A01N 27/00 |
| WO | 2011004450 A1 | 8/2011 | | |
| WO | WO-2011094450 A1 ‡ | 8/2011 | ............ | C07F 5/025 |
| WO | 2014/145189 A1 | 9/2014 | | |
| WO | WO-2014/145189 A1 ‡ | 9/2014 | ............ | A01N 43/42 |
| WO | WO-2014145189 A1 ‡ | 9/2014 | ............ | A01N 43/42 |

OTHER PUBLICATIONS

Nathanson, James A. "Caffeine and related methylxanthines: possible naturally occurring pesticides." Science 226.4671 (1984): 184-187. (Year: 1984).*
Bascal, Z. A., et al. "Characterization of a putative nitric oxide synthase in the neuromuscular system of the parasitic nematode, Ascaris suum." Parasitology 122.2 (2001): 219-231. (Year: 2001).*
O'Halloran, D.M. et al., "Changes in cGMP levels affect the localization of EGL-4 in AWC in Caenorhabditis elegans", PLoS One, Feb. 2012, vol. 7, pp. 1-12.‡
Ramot, D. et al., "The Parallel Worm Tracker: a platform for measuring average speed and drug-induced paralysis in nematodes", PLoS One, May 2008, vol. 3, pp. 1-7.‡
Talavera, M. and T. Mizukubo, "Effects of DL-methionine on hatching and activity of Meloidogyne incognita eggs and juveniles", Pest. Manag. Sci., Apr. 2005, vol. 61, pp. 413-416.‡
Wang, C. et al., "Application of Pluronic gel to the study of root-knot nematode behavior", J.Nematol., 2009, vol. 11, pp. 453-464.‡
Matsuura,T. et al., "Enhancement of chemotactic response to sodium acetate in the nematode Caenorhabditis elegans", Zoolog. Sci., Aug. 2010, vol. 27, pp. 629-637.‡
Nitao, J. K. et al., "In-vitro assays of Meloidogyne incognita and Heterodera glycines for detection of nematode-antagonistic fungal compounds", J. Nematol., Jun. 1999, vol. 31, pp. 172-183.‡
Lin, C. H. et al., "Dynamic and persistent effects of ethanol exposure on development: an in vivo analysis during and after embryonic ethanol exposure in Caenorhabditis elegans", Alcohol Clin. Exp. Res., Jan. 2013, vol. 37, pp. E190-E198.‡

(Continued)

*Primary Examiner* — Robert J Yamasaki
(74) *Attorney, Agent, or Firm* — Pierce Atwood LLP

(57) ABSTRACT

The invention relates, in part, to methods to identify compounds to treat a phytoparasitic nematode infection and/or reduce phytoparasitic nematode contamination, and to methods and compositions to treat phytoparasitic nematode infections and to reduce phytoparasitic nematode contamination of a substrate such as, but not limited to: a plant, agricultural medium, or soil.

5 Claims, 12 Drawing Sheets

Specification includes a Sequence Listing.

(56) References Cited

OTHER PUBLICATIONS

Lugnier, C., "Cyclic nucleotide phosphodiesterase (PDE) superfamily: A new target for the development of specific therapeutic agents", Pharmacol. Ther., Mar. 2006, vol. 109, pp. 366-398.‡
Osman et al., "Efficacy of Biologically Active Agents as Nontraditional Nematicides for Meloidogyne javanica", Revue Nematol., 1988, vol. 11, pp. 93-98.‡
Schuster, K. et al., "PDE inhibitors as potential pesticides targeting parasitic nematodes", The FASEB Journal, Meeting Abstract Supplement, Apr. 2013, vol. 27, p. 1052.6.‡
Taylor, C. et al., "Discovery of Anthelmintic Drug Targets and Drugs Using Chokepoints in Nematode Metabolic Pathways", PLOS Pathogens, Aug. 2013, vol. 9, 17 pages.‡
Usuyama, M. et al., "A Model of the Intracellular Response of an Olfactory Neuron in Caenorhabditis elegans to Odor Stimulation", PLoS One, Aug. 2012, vol. 7, 9 pages.‡
Cappello, M. et al., "A purified Bacillus thuringiensis crystal protein with therapeutic activity against the hookworm parasite *Ancylostoma ceylanicum*", Proc. natl. Acad. Sci. U. S. A., Oct. 2006, vol. 103, pp. 15154-15159.‡
Hollingworth, R.M. and L.L. Murdock, "Formamidine pesticides: octopamine-like actions in a firefly", Science, Apr. 1980, vol. 208, pp. 74-76.‡
Ward, S., "Chemotaxis by the nematode Caenorhabditis elegans: identification of attractants and analysis of the response by use of mutants", Proc. Natl. Acad. Sci. U. S. A., Mar. 1973, vol. 70, pp. 817-821.‡
Zhang, X. et al., "Efficacy and selectivity of phosphodiesterase-targeted drugs in inhibiting photoreceptor phosphodiesterase (PDE6) in retinal photoreceptors", Invest. Ophthalmol. Vis. Sci., Sep. 2005, vol. 46, pp. 3060-3066.‡
Francis, S. H. et al., "Mammalian cyclic nucleotide phosphodiesterases: molecular mechanisms and physiological functions", Physiological Reviews, Apr. 1, 2011, vol. 91, pp. 651-690.‡
Fudali, S. L. et al., "Ethylene signaling pathway modulates attractiveness of host roots to the root-knot nematode *Meloidogyne hapla*", Molecular Plant-Microbe Interactions, Jan. 2013, vol. 26, pp. 75-86.‡
Cote, R. H., "Kinetics and regulation of cGMP binding to noncatalytic binding sites on photoreceptor phosphodiesterase", Methods Enzymol., 2000, vol. 315, pp. 646-672.‡
D'Amours, M. R. et al., "Potency and mechanism of action of E4021, a type 5 phosphodiesterase isozyme-selective inhibitor, on the photoreceptor phosphodiesterase depend on the state of activation of the enzyme", Mol. Pharmacol., Mar. 1999, vol. 55, pp. 508-514.‡
L'Etoile, N. D. et al., "The cyclic GMP-dependent protein kinase EGL-4 regulates olfactory adaptation in C. elegans", Neuron, Dec. 19, 2002, vol. 36, pp. 1079-1089.‡
Lichtarge, O. and M.E. Sowa, "Evolutionary predictions of binding surfaces and interactions", Curr. Opin. Struct. Biol., Feb. 2002, vol. 12, pp. 21-27.‡
Handoo, Z. A. "Plant-parastic nematodes", USDA Agricultural Research Service, 1998, 10 pages.‡
Kano, T. et al., "Memory in Caenorhabditis elegans is mediated by NMDA-type ionotropic glutamate receptors", Current Biology, Jul. 8, 2008, vol. 18, pp. 1010-1015.‡
Brenner, S., "The genetics of Caenorhabditis elegans", Genetics, May 1974, vol. 77, pp. 71-94.‡
Burgin, A. B. et al., "Design of phosphodiesterase 4D (PDE4D) allosteric modulators for enhancing cognition with improved safety", Nat. Biotechnol., Jan. 2010, vol. 28, pp. 63-70.‡
Cahill, K. B. et al., "Identification of amino acid residues responsible for the selectivity of tadalafil binding to two closely related phosphodiesterases, PDE5 and PDE6", J. Biol. Chem., Nov. 30, 2012, vol. 287, pp. 41406-41416.‡
Carleton, K. L. et al., "Rod and cone opsin families differ in spectral tuning domains but not signal transducing domains as judged by saturated evolutionary trace analysis", J. Mol. Evol., Jul. 2005, vol. 61, pp. 75-89.‡
Barker, K. R. et al., "Plant and Soil Nematodes: Societal Impact and Focus for the Future", The Journal of Nematology, Jun. 1994, vol. 26, pp. 127-137.‡
Bender, A. T. and J. A. Beavo, "Cyclic nucleotide phosphodiesterases: molecular regulation to clinical use", Pharmacol. Rev., Sep. 2006, vol. 58, pp. 488-520.‡
Wormbase. WormBase web site, www.wormbase.org, release WS235, 2013, 8 pages.‡
Bargmann, C. I. et al, "Odorant-selective genes and neurons mediate olfaction in C. elegans", Cell, Aug. 13, 1993, vol. 74, pp. 515-527.‡
European Search Report received for European Application No. 14763827.4 dated Nov. 16, 2016, 10 pages.‡
International Search Report and Written Opinion dated Aug. 2, 2014 from corresponding PCT/US2014/029910 filed on Mar. 15, 2014.‡
Satou et al., Veterinary Parasitology, 104, pp. 131-138. (Year: 2002).‡
Radewald et al., The importance of soil fumigation for nematode control, California Agriculture, 1987, pp. 16-17. (Year: 1987).‡
Bender, A. T. et al., "Cyclic nucleotide phosphodiesterases: molecular regulation to clinical use", Pharmacol. Rev., Sep. 2006, vol. 58, pp. 488-520.
Burgin, A. B. et al., "Design of phosphodiesterase 4D (PDE4D) allosteric modulators for enhancing cognition with mproved safety", Nat. Biotechnol., Jan. 2010, vol. 28, pp. 63-70.
Cahill, K. B. et al., "Identification of amino acid residues responsible for the selectivity of tadalafil binding to two closely related phosphodiesterases, PDE5 and PDE6", J. Biol. Chem., Nov. 30, 2012, vol. 287, pp. 1406-41416.
Cappello, M. et al., "A purified Bacillus thuringiensis crystal protein with therapeutic activity against the hookworm oarasite *Ancylostoma ceylanicum*", Proc. Natl. Acad. Sci. USA., Oct. 2006, vol. 103, pp. 15154-15159.
Carleton, K. L. et al., "Rod and cone opsin families differ in spectral tuning domains but not signal transducing domains as judged by saturated evolutionary trace analysis", J. Mal.Evol., Jul. 2005, vol. 61, pp. 75-89.
Cote, R.H., "Kinetics and regulation of cGMP binding to noncatalytic binding sites on photoreceptor chosphodiesterase", Methods Enzymol., 2000, vol. 315, pp. 646-672.
D'Amours, M. R. et al., "Potency and mechanism of action of E4021, a type 5 phosphodiesterase isozyme-selective onhibitor, on the photoreceptor phosphodiesterase depend on the state of activation of the enzyme", Mal. Pharmaool., Mar. 1999, vol. 55, pp. 508-514.
Hollingworth, RM.et al., "Formamidine pesticides: octopamine-like actions in a firefly", Science, Apr. 1980, vol. 208, pp. 74-76.
Kano, T. et al., "Memory in Caenorhabditis elegans is mediated by NMDA-type ionotropic glutamate receptors", Current Biology, Jul. 8, 2008, vol. 18, pp. 1010.
Lichtarge, 0. and M.E. Sowa, "Evolutionary predictions of binding surfaces and interactions", Curr. Opin. Struct. I., Feb. 2002, vol. 12, pp. 21-27.
Lin, C.H. et al., "Dynamic and persistent effects of ethanol exposure on development: an in vivo analysis during and lifter embryonic ethanol exposure in Caenorhabditis elegans", Alcohol Clin. Exp. Res., Jan. 2013, vol. 37, pp. E190-E198.
Lugnier, C., "Cyclic nucleotide phosphodiesterase (PDE) superfamily: A new target for the development of specific herapeutic agents", Pharmacol. Ther., Mar. 2006, vol. 109, pp. 366-398.
Matsuura,T. et al., "Enhancement of chemotactic response to sodium acetate in the nematode Caenorhabditis s elegans", Zoolog. Sci., Aug. 2010, vol. 27, pp. 629-637.
Zhang, X. et al., "Efficacy and selectivity of phosphodiesterase-targeted drugs in inhibiting photoreceptor chosphodiesterase (PDE6) in retinal photoreceptors", Invest. Ophthalmol. Vis. Sci., Sep. 2005, vol. 46, pp. 3060-3066.

\* cited by examiner
‡ imported from a related application

Accession numbers for proteins used to generate phylogenetic tree for PDE families

| PDE1 | PDE2 | PDE3 | PDE4 | PDE10 (nematode PDE-5) | PDE8 (nematode PDE-6) |
|---|---|---|---|---|---|
| EDL86779 | XP 851951.2 | NP 001231612.1 | ENSGACP00000025810 | NP 491544.3 | NP 002596 |
| XP 852114.2 | EDM18280.1 | CAF99655.1 | AAA41101.1 | XP 002939024.1 | NP 942062.1 |
| NP 776840.1 | NP 001243202.1 | NP 035185.2 | XP 003432831.2 | NP 957396.1 | XP 545870.3 |
| NP 001009979.1 | AAH06845.1 | XP 003968538.1 | Aa 18117.1 | XP 003964260.1 | XP 003586548.1 |
| XP 001372011.2 | 3182954 | XP 618666.4 | bae36041.1 | CAG09487.1 | NP 032829.1 |
| xp 001515772.2 | XP 003449362.1 | XP 003341503.1 | xp 001381247.2 | NP006652 | XP 001362180.2 |
| NP 000915 | XP 003977061.1 | NP 059033.1 | q08499 | XP 0015061 07.2 | XP 003428258.1 |
| CAG07077.1 | NP 001072607.1 | XP 853486.2 | xp 003972415.1 | AAD31544.1 | CAF99802.1 |
| XP 692892.5 | ENSGACP00000010240 | XP 793920.3 | xp 693630.3 | XP 582454.3 | XP 003969918.1 |
| NP 001096444.4 | NP 001022706.2 | XP 691883.3 | xp 002939717.1 | XP 541190.3 | XP 001920432.3 |
| NP 001236974.2 | XP 798824.3 | NP 001026353.1 | XP 003643033.1 | AAs21246.1 | XP 002940924.1 |
| NP 001129790.1 | XP 396028.4 | ENSGACP00000013254 | np 871945.1 | XP 419613.3 | NP 490787.1 |
| NP 609520.1 | | | NP 726859.2 | XP 794212.3 | XP 392234.3 |
| NP 001091918.1 | | | xp 394762.4 | XP 394107.3 | XP 003725794.1 |
| XP 001120223.2 | | | xp 003724002.1 | | NP 726353.1 |
| XP 003976081.1 | | | | | |

FIG. 3

| A.A. Residue Number (Alignment sequence) | 419 | 422 | 436 | 475 | 478 |
|---|---|---|---|---|---|
| Nematode PDE 2 | L | Q | I | Q | F |
| Vertebrate PDE 2 | L | Q | I | Q | F |
| PDE2 IBMX Interactions | L | Q | I | Q | F |

| A.A. Residue Number (Alignment sequence) | 176 | 177 | 357 | 419 | 420 | 421 | 422 | 429 | 431 | 432 | 433 | 436 | 444 | 461 | 462 | 463 | 474 | 475 | 477 | 478 |
|---|---|---|---|---|---|---|---|---|---|---|---|---|---|---|---|---|---|---|---|---|
| Meloidogyne hapla PDE3 | L | L | | | N | S | P | H | Q | W | T | | F | P | Y | M | L | Q | S | F |
| Caenorhabditis spp. PDE3 | Y | L | | | N | S | P | H | Q | W | T | | F | P | Y | M | L | Q | S | F |
| Vertebrate PDE3 | Y | L | | | N | G | P | H | KQR | W | T | | F | P | F | M | L | Q | S | F |
| PDE3-IBMX Interactions | Y | L | | | | | | | | | | | F | | | | | Q | | |
| PDE3-Merck Interactions | | | | | N | G | P | H | KQR | W | T | | F | P | F | M | L | Q | S | F |

| A.A. Residue Number (Alignment sequence) | 176 | 177 | 181 | 275 | 355 | 356 | 418 | 419 | 421 | 422 | 429 | 432 | 433 | 436 | 437 | 444 | 456 | 462 | 475 | 478 |
|---|---|---|---|---|---|---|---|---|---|---|---|---|---|---|---|---|---|---|---|---|
| Meloidogyne Hapla PDE4 | Y | H | H | D | T | M | D | L | N | P | Y | W | N | I | L | Y | L | M | Q | F |
| Caenorhabditis spp PDE4 | Y | H | H | D | T | M | D | L | N | P | Y | W | N | I | M | Y | L | M | Q | F |
| Vertebrate PDE4 | Y | H | H | D | T | M | D | L | N | P | Y | W | T | I | ILM | F | LM | M | Q | F |
| PDE4-IBMX Interactions | | | | | | M | | | N | | | | | | | | M | M | Q | F |
| PDE4-Roflumilast Interactions | | H | | | T | M | D | L | N | P | Y | W | T | I | M | | M | | Q | F |
| PDE54-Zardaverine Interactions | | H | | D | | | | | N | P | Y | W | T | I | | F | M | | Q | F |
| PDE4-Rolipram Interactions | Y | | | | | | | | N | | Y | | T | I | M | F | | | Q | F |

| A.A. Residue Number (Alignment sequence) | 357 | 437 | 444 | 475 | 478 |
|---|---|---|---|---|---|
| Meloidogyne hapla PDE5 | L | F | F | Q | F |
| Caenorhabditis spp. PDE5 | L | F | F | Q | F |
| Vertebrate PDE10 | L | Y | F | Q | F |
| PDE410-Papaverine Interactions | L | Y | F | Q | F |

FIG. 4

|  | PDE2 IBMX | PDE3B-IBMX | PDE3B-Merck | PDE4D Roflumilast | PDE4D Rolipram | PDE4D-IBMX | PDE4D Zardaverine | PDE10 Papaverine |
|---|---|---|---|---|---|---|---|---|
|  | L809 | Y736 | 938-941 | H406 | Y405 | Met273 | H462 | 696 |
|  | Q812 | H737 | H948 | T517 | N567 | Asn321 | H466 | 726 |
|  | I826 | L895 | 950-952 | M519 | Y575 | Ile336 | D503 | 729 |
|  | Q859 | I955 | I955 | D564 | T579 | Phe340 | D620 |  |
|  | F862 | F959 | F959 | L565 | I582 | Met357 | N623 |  |
|  |  | Q988 | P975 | N567 | M583 | Phe372 | P624 |  |
|  |  | F991 | F976 | Y575 | F586 | Ile376 | Y631 |  |
|  |  |  | M977 | T579 | Q615 |  | W634 |  |
|  |  |  | L987 | I582 | F618 |  | T635 |  |
|  |  |  | Q988 | M583 |  |  | I638 |  |
|  |  |  | S990 | M603 |  |  | F642 |  |
|  |  |  | F991 | Q615 |  |  | M659 |  |
|  |  |  | W1072 | F618 |  |  | Q671 |  |
|  |  |  |  |  |  |  | F674 |  |
| Accession number | NP 000408 | NP 000913 | NP 000913 | NP 006194 | NP 006194 | NP 006194 | NP 006194 | NP 006652 |
| PDB structure file | 3ITU | 1SOJ | 1SO2 | 1XOQ | 1XMY | 1ZKN | 1XOR | 4AEL |

```
MHA PDE3    --------------------------------------------------
HGL PDE3    DRAELERDPALGQIQEWSFPIFRLAEKHKRTVSRLTYAIFKEADLFRTFK  50
CEL PDE3    --------------------------------------------------
HSA PDE3A   -----------------------------------------DMGLFEAFK   9

MHA PDE3    ------------------DIP-HNRIHAADVLHGCFYLTCHAVQAFY---  28
HGL PDE3    ISYTKFFNFFHALESGYWDIPYHNRIHAADVLHGTYYLTCHPVHAFCRQM 100
CEL PDE3    -----------------------------SSIMSQLSTLE----------  11
HSA PDE3A   IPIREFMNYFHALEIGYRDIPYHNRIHATDVLHAVWYLTTQPIPGLSTVI  59
                               :.::       *

MHA PDE3    ----------------------------------------------LMAL  32
HGL PDE3    ----------------------------PFDFGNYIESILKNSFVPLMAL 122
CEL PDE3    ----------------------------------------------LMAL  15
HSA PDE3A   NDHGSTSDSDSDSGFTHGHMGYVFSKTYNVTDDKYGCLSGNIPALELMAL 109
                                                          ****

MHA PDE3    FSAAAMHDYDHPGRTNAFLVASEDKKAILYNDRSVLENHHAAESWKLLTS  82
HGL PDE3    YTAAAMHDYDHPGRTNAFLVASEDRKAILYNDRSVLENHHAAESWRLLNS 172
CEL PDE3    FTAAAMHDYDHPGRTNAFLVQVEDKKAILYNDRSVLENHHAAESWKLLN-  64
HSA PDE3A   YVAAAMHDYDHPGRTNAFLVATSAPQAVLYNDRSVLENHHAAAAWNLFMS 159
            : ******************  .  .:*:************** :*.*:

MHA PDE3    QSSYNFIESLDSAETKRFFRYLVLEYILATDLKQHFDIIVQFNERAPS-- 130
HGL PDE3    HAQFQFIENLDSAETKR-FRYLVLEYILATDLKQHFDIIMQFNERVPD-- 219
CEL PDE3    KPENHFIENLDPAEMKR-FRYLVLEYILATDLKQHFEIIMTFTERLTE-- 111
HSA PDE3A   RPEYNFLINLDHVEFKH-FRFLVIEAILATDLKKHFDFVAKFNGKVNDDV 208
            :... :*: .** .* *: **:**:*.********:**::: *.: .

MHA PDE3    -MDLSNESDRMLISLMIIKFADINSPAKPYSLHKQWTERICQEFYEQGDE 179
HGL PDE3    -MDLNSESDRVLISLMLIN-----------------LICQEFYEQGDD 249
CEL PDE3    -IDVQVETDRLLIGKLLIKMADINSPTKPYGLHRQWTDRICEEFYEQGDD 160
HSA PDE3A   GIDWTNENDRLLVCQMCIKLADINGPAKCKELHLQWTDGIVNEFYEQGDE 258
             :*     *.**:*:    : *:             * :*******:

MHA PDE3    ERLRNMAISPYMDRSEPAVAKLQDSFIAHIVNPLAIALNEANLLP----- 224
HGL PDE3    EKRRKMPVSPYMDRNEPAVAKLQDSFIAHIVNPLAIALNEAGLFP----- 294
CEL PDE3    ERRRGLPITPYMDRGDAQVAKLQDSFIAHVVSPLATAMNECGLLP----- 205
HSA PDE3A   EASLGLPISPFMDRSAPQLANLQESFISHIVGPLCNSYDSAGLMPGKWVE 308
            *    :..::*.***.   .:*:**:**:**.  . : :...*:*

MHA PDE3    ---------------ILPGLPES--------------------G 233
HGL PDE3    ---------------VLPGLPESE-------------------LIIN 307
CEL PDE3    ---------------ILPGLDTSE-------------------LIIN 218
HSA PDE3A   DSDESGDTDDPEEEEEAPAPNEEETCENNESPKKKTFKRRKIYCQITQH 358
                            *.  .

MHA PDE3    LRHNHQKWLNQIEFDQ--KHCRESEEDEKRGNALGNNKTNISR------- 274
HGL PDE3    LKHNHQKWLHQ--------------------------------------- 318
CEL PDE3    MEHNHRKWKEQIELEN--GGSYEAQITCNGGTAVNGVIEEESASTSDSPD 266
HSA PDE3A   LLQNHKMWKKVIEEEQRLAGIENQSLDQTPQSHSSEQIQAIKEEEEEKGK 408
            : :**: * .

MHA PDE3    --------------
HGL PDE3    --------------
CEL PDE3    PRRDSPLDSDLSQ 279
HSA PDE3A   PRGEEIPTQKPDQ 421
```

FIG. 16

METHODS OF IDENTIFICATION AND USE OF NEMATICIDE COMPOUNDS

RELATED APPLICATIONS

This application is a divisional of US patent application Ser. No. 14/776,827, filed Sep. 15, 2015, which was the National Stage Filing under U.S.C. §371 of PCT to International Application PCT/US2014/29910, filed Mar. 15, 2014, which claims benefit under 35 U.S.C. § 119(e) of U.S. Provisional Application No. 61/793,374, filed Mar. 15, 2013, and-the content of each of which is incorporated by reference herein in its entirety.

GOVERNMENT INTEREST

This invention was made with government support under the Hatch grant NH00568 awarded by the United States Department of Agriculture (USDA). The Government has certain rights in the invention.

FIELD OF THE INVENTION

The invention relates, in part, to nematicide compositions and methods of their identification and methods of their use to control phytoparasitic nematode infections and contamination.

BACKGROUND

Plant-parasitic nematodes are a major cause of reduced agricultural productivity worldwide, resulting in an estimated $80-100 billion dollars in crop damage annually [Barker et al., (1994), Handoo, (1998)]. Current measures to control damage from phytoparasitic nematodes falls into three major categories: (a) biological controls (e.g., genetic engineering of plants to increase resistance to nematode attack, or introduction of organisms that target nematodes), (b) agricultural practices (e.g., crop rotation, intercropping), and (c) application of chemical pesticides. These traditional approaches have been only partially successful in reducing nematode damage to crops.

SUMMARY OF THE INVENTION

The invention in part, provides methods to identify candidate compounds that reduce activity of phytoparasitic nematodes, and also provides methods and compositions to treat such infections and contamination by a phytoparasitic nematode.

According to an aspect of the invention, methods of identifying a candidate phytoparasitic nematode phosphodiesterase (PDE) inhibitor compound that disrupts cyclic nucleotide metabolism in a phytoparasitic nematode are provided. The methods include a) contacting a phytoparasitic nematode test sample with a test compound under conditions suitable for PDE activity; b) measuring the level of PDE activity in the test sample; c) comparing the measured level of PDE activity in the test sample to a control level of PDE activity; and d) determining whether the contacted test sample has a reduced level of PDE activity relative to the control level of PDE activity, wherein a reduced level of PDE activity in the test sample relative to the control level of PDE activity identifies the test compound as a candidate phytoparasitic nematode PDE inhibitor compound that disrupts cyclic nucleotide metabolism in the phytoparasitic nematode. In some embodiments, the control level is a level PDE of activity determined in a phytoparasitic nematode sample under conditions suitable for PDE activity and not contacted with the test compound. In certain embodiments, the control comprises a vertebrate sample contacted with the candidate compound under suitable conditions for PDE activity in the vertebrate sample, and wherein a reduction in PDE activity in the test sample relative to the control sample further identifies the test compound as selectively disrupting cyclic nucleotide metabolism in the phytoparasitic nematode compared to the vertebrate. In some embodiments, the vertebrate PDE is an ortholog of the phytoparasitic nematode PDE. In some embodiments, the control comprises a non-phytoparasitic nematode sample contacted with the test compound under suitable conditions for PDE activity in the non-phytoparasitic nematode sample, and wherein a reduction in the level of PDE activity in the test sample relative to the level of PDE activity in the control sample further identifies the test compound as selectively disrupting cyclic nucleotide metabolism in the phytoparasitic nematode compared to the non-phytoparasitic nematode. In certain embodiments, the non-phytoparasitic nematode PDE is a PDE ortholog of the phytoparasitic nematode PDE. In some embodiments, the sample comprises one or more cells. In certain embodiments, the test sample is an in vitro or an in vivo sample. In some embodiments, the control sample is an in vivo or an in vitro sample. In some embodiments, the candidate compound is a compound that selectively binds a catalytic binding site of a phytoparasitic nematode PDE as compared to its binding to the corresponding catalytic binding site of a non-parasitic nematode PDE ortholog and/or a vertebrate PDE ortholog. In some embodiments, the method also includes determining one or more amino acid differences between a sequence of a catalytic domain of the phytoparasitic nematode PDE and a sequence of the corresponding catalytic domain of a non-phytoparasitic nematode PDE ortholog or a vertebrate PDE ortholog; and selecting the test compound based at least in part on the one or more identified differences between the catalytic domain sequences. In certain embodiments, disrupting cyclic nucleotide metabolism in the phytoparasitic nematode reduces an activity of a phytoparasitic nematode. In some embodiments, the activity of the phytoparasitic nematode is development, hatching, transition from one life-cycle stage to another life-cycle stage, chemosensation, chemotaxis, locomotion, invasion of a host, replication, reproduction, viability, infectivity, or establishment of a parasitic interaction with a host. In some embodiments, the phytoparasitic nematode is an embryonic-stage nematode, a juvenile-stage nematode, or an adult-stage nematode. In certain embodiments, the phytoparasitic nematode is a *Heterodera* spp., *Pratylenchus* spp., *Globodera* spp., *Meliodogyne* spp., *Radopholus* ssp., or *Xiphinema* ssp. nematode.

According to another aspect of the invention, methods of reducing an activity of a phytoparasitic nematode, the method comprising contacting the phytoparasitic nematode with a selective phytoparasitic nematode phosphodiesterase (PDE) inhibitor in an amount effective to reduce an activity of the phytoparasitic nematode. In some embodiments, contacting a vertebrate sample with the selective phytoparasitic nematode PDE inhibitor under conditions suitable for PDE inhibition in the vertebrate sample does not result in a significant negative effect on a biological function of the vertebrate sample. In some embodiments, contacting a vertebrate sample with the selective phytoparasitic nematode PDE inhibitor under conditions suitable for PDE inhibition in the vertebrate sample does not result in a significant level of PDE inhibition in the vertebrate sample. In certain embodiments, the selective phytoparasitic nematode PDE inhibitor is more effective at inhibiting a phytoparasitic nematode PDE than inhibiting a vertebrate ortholog PDE. In some embodiments, the vertebrate sample comprises a vertebrate cell, tissue, or organism. In some embodiments, the activity of the phytoparasitic nematode is development, hatching, transition from one life-cycle stage to another life-cycle stage, chemosensation, chemotaxis, locomotion, infectivity, viability, reproduction, replication, invasion of a host, or establishment of a parasitic interaction with a host. In some embodiments, the nematode is an embryonic-stage nematode, a juvenile-stage nematode, or an adult-stage nematode. In certain embodiments, the phytoparasitic nematode is a *Heterodera* spp., *Pratylenchus* spp., *Globodera* spp., *Meliodogyne* spp., *Radopholus* ssp., or *Xiphinema* ssp. nematode. In some embodiments, the phytoparasitic nematode PDE is an ortholog of a vertebrate PDE. In some embodiments, under suitable conditions for PDE inhibition, the selective phytoparasitic nematode PDE inhibitor has a higher level of inhibitory activity against the phytoparasitic nematode PDE than against the vertebrate PDE ortholog. In certain embodiments, contact of the vertebrate PDE ortholog with the selective phytoparasitic nematode PDE inhibitor under suitable conditions for PDE inhibition, results in a level of inhibition of the vertebrate PDE ortholog of less than zero, or less than 20%, 30%, 40%, 50%, 60%, 70%, 80%, 90%, or 100% of the level of inhibition of the phytoparasitic nematode PDE contacted by the selective phytoparasitic nematode PDE inhibitor under suitable conditions for PDE inhibition. In some embodiments, level of inhibition of the vertebrate PDE ortholog of less than zero, or less than 20%, 30%, 40%, or 50%, of the level of inhibition of the phytoparasitic nematode PDE contacted by the selective phytoparasitic nematode PDE inhibitor under suitable conditions for PDE inhibition. In some embodiments, the phytoparasitic nematode PDE is an ortholog of a non-phytoparasitic nematode PDE. In certain embodiments, the non-phytoparasitic nematode is a *C. elegans*. In some embodiments, under suitable conditions for PDE inhibition, the selective phytoparasitic nematode PDE inhibitor has a higher level of inhibitory activity against the phytoparasitic nematode PDE than against the non-phytoparasitic nematode PDE ortholog. In some embodiments, contact of the non-phytoparasitic nematode PDE ortholog with the selective phytoparasitic nematode PDE inhibitor under suitable conditions for PDE inhibition, results in a level of inhibition of the non-phytoparasitic nematode PDE ortholog of zero, or less than 20%, 30%, 40%, 50%, 60%, 70%, 80%, 90%, 99%, or 100% of the level of inhibition of the phytoparasitic nematode PDE contacted by the selective phytoparasitic nematode PDE inhibitor under suitable conditions for PDE inhibition. In certain embodiments, the phytoparasitic nematode is additionally contacted with one or more additional anti-phytoparasitic agents, wherein the selective PDE inhibitor and the additional agent act synergistically to reduce the activity of the phytoparasitic nematode. In some embodiments, the additional anti-phytoparasitic agent is a pesticide fumigant or a compound that stimulates synthesis of cyclic nucleotides.

According to yet another aspect of the invention, compositions comprising a phytoparasitic nematode phosphodiesterase (PDE) inhibitor compound and an additional anti-phytoparasitic-nematode agent are provided. In some embodiments, the PDE inhibitor compound is a PDE inhibitor that when contacted with a vertebrate control does not result in a significant negative effect on a biological function of the vertebrate control. In certain embodiments, the additional anti-phytoparasitic-nematode agent is a pesticide fumigant or a compound that stimulates synthesis of cyclic nucleotides. In some embodiments, the phytoparasitic nematode is a *Heterodera* spp., *Pratylenchus* spp., *Globodera* spp., *Meliodogyne* spp., *Radopholus* ssp., or *Xiphinema* ssp. nematode.

According to another aspect of the invention, methods of decontaminating a substrate that has or is at risk of having phytoparasitic nematode contamination are provided. The methods include contacting the substrate with one or more selective phytoparasitic nematode phosphodiesterase (PDE) inhibitors in an amount effective to reduce the phytoparasitic nematode contamination of, or risk of phytoparasitic nematode contamination of, the substrate. In some embodiments, the phytoparasitic nematode is a *Heterodera* spp., *Pratylenchus* spp., *Globodera* spp., *Meliodogyne* spp., *Radopholus* ssp., or *Xiphinema* ssp. nematode. In certain embodiments, the phytoparasitic nematode is an embryonic-stage nematode, a juvenile-stage nematode, or an adult-stage nematode. In some embodiments, reducing the phytoparasitic nematode contamination of the substrate comprises reducing the viability of and/or infectivity of the one or more phytoparasitic nematodes in or on the substrate. In some embodiments, the substrate comprises a plant, a portion of a plant, soil, fertilizer, manure, peat, loam, vermiculite, an agricultural medium, or a planting medium. In some embodiments, the contaminated substrate comprises or is likely to comprise one or more phytoparasitic nematodes. In certain embodiments, the substrate is contacted by an aqueous composition comprising the selective phytoparasitic nematode PDE inhibiting compound.

According to another aspect of the invention, methods of treating a phytoparasitic nematode infection in a plant are provided. The methods including: administering to a plant having, or at risk of having, a phytoparasitic nematode infection an effective amount of at least one selective phytoparasitic nematode phosphodiesterase (PDE) inhibitor to treat the phytoparasitic nematode infection. In some embodiments, contacting a vertebrate control with the amount of the selective PDE inhibitor does not result in a significant negative effect on a biological function of the vertebrate control. In some embodiments, the infection is a *Heterodera* spp. nematode infection, *Pratylenchus* spp. nematode infection, *Globodera* spp. nematode infection, *Meliodogyne* spp. nematode infection, *Radopholus* ssp. nematode infection, or *Xiphinema* nematode infection. In certain embodiments, the parasitic nematode infection comprises the presence of one or more parasitic nematodes in the plant, on the plant, or in the environment of the plant. In some embodiments, the parasitic nematode is an embryonic-stage nematode, a juvenile-stage nematode, or an adult-stage nematode. In some embodiments, the method also includes administering one or more additional nematicides to the plant and/or the environment of the plant. In certain embodiments, the environment of the plant comprises the substrate in which the plant is growing or will be grown. In some embodiments, the treatment is a prophylactic treatment.

According to another aspect of the invention, kits are provided. The kits may include, a first container housing a phytoparasitic nematode phosphodiesterase (PDE) inhibitor, a second container housing a second nematicide compound, and instructions for administering the inhibitor and the nematicide compound to a substrate having or at risk of having a phytoparasitic nematode infection or contamination. In certain embodiments, the infection is a *Heterodera* spp. nematode infection, *Pratylenchus* spp. nematode infection, *Globodera* spp. nematode infection, *Meliodogyne* spp. nematode infection, *Radopholus* ssp. nematode infection, or *Xiphinema* ssp. nematode infection. In some embodiments, the parasitic nematode infection comprises the presence of an embryonic-stage nematode, a juvenile-stage nematode, or an adult-stage nematode in or on the plant. In some embodiments, the kit also includes instructions to administer one or more additional phytoparasitic nematode PDE inhibitor compounds and/or a nematicide compound to the substrate. In certain embodiments, the substrate comprises a plant, a portion of a plant, soil, fertilizer, manure, peat, loam, vermiculite, an agricultural medium, or a planting medium.

The present invention is not intended to be limited to a system or method that must satisfy one or more of any stated objects or features of the invention. It is also important to note that the present invention is not limited to the exemplary or primary embodiments described herein. Modifications and substitutions by one of ordinary skill in the art are considered to be within the scope of the present invention.

BRIEF DESCRIPTION OF THE DRAWINGS

FIG. 3 provides a table of accession numbers for proteins used to generate the phylogenetic tree for PDE families for PDE1, PDE2, PDE3, PDE4, PDE10 (nematode PDE-5) and PDE8 (nematode PDE-6. Omitted from FIG. 3 are accession numbers for proteins from those five PDE families that are not present in nematode genomes.

FIG. 4 shows results of alignments of saturated evolutionary trace analysis that was used to identify unanimous sites (identical amino acid in every vertebrate and invertebrate sequence analyzed) and class-specific sites (an invariant amino acid in every vertebrate sequence within a PDE family and a different, invariant amino acid present in every nematode sequence of the same PDE family). Groups of identifiers [e.g., nematode, vertebrate, 3-isobutyl-1-methylxanthine (IBMX) interactions, and PDE family] are listed on the left, residues are shown and specific differences between residues at locations are shown. Two boxes in residues for *M. hapla* indicate residues that are different for *M. hapla* compared to the corresponding residue in *Caenorhabditis* spp. These boxes are the first box in PDE3 (L) and the second box in PDE4 (L) and these boxes indicate a residue at a position only in *Meliodogyne hapla*. The remaining boxes shown in FIG. 4 indicate a residue at a position that is only in *Meliodogyne hapla* and *Caenorhabditis* spp.

FIG. 16 shows a sequence alignment of the PDE3 amino acid sequences from *Meloidogyne hapla* [MHA PDE3 (SEQ ID NO:1), contig 894], *Heterodera glycines* [HGL PDE3 (SEQ ID NO:2), U.S. Pat. No. 8,067,671 sequence 143193], *Caenorhabditis elegans* [CEL PDE3 (SEQ ID NO:3), Accession number NP 001254453], and *Homo sapiens* [HSA PDE3 (SEQ ID NO:4), Accession number NP 000913].

DETAILED DESCRIPTION

Figure 1:
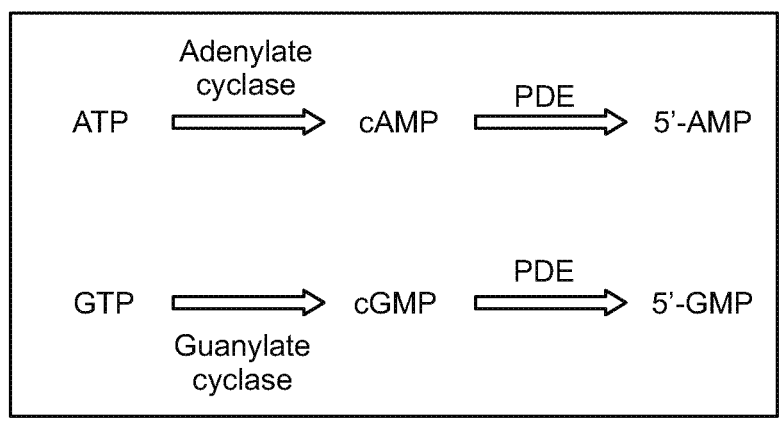
FIG. 1 provides a diagram of enzymes responsible for regulating the levels of cyclic nucleotides in cells. PDE=phosphodiesterase; ATP=adenosine triphosphate; GTP=guanosine triphosphate; 5'-AMP=5'-adenosine monophosphate; 5'-GMP=5'-guanosine monophosphate; cAMP=cyclic adenosine monosphosphate; and cGMP=cyclic guanosine monophosphate.

It has now been identified that PDE inhibitor compounds can be used in methods to treat phytoparasitic nematode infections in plants and to treat phytoparasitic nematode contamination of substrates. In certain aspects of the invention, methods of identifying compounds that function as phytoparasitic nematode PDE inhibitors are provided. The invention also provides in some aspects, in vitro and/or in vivo methods useful to characterize one or more compounds to determine whether or not they may be useful to treat a phytoparasitic nematode infection or to reduce or eliminate contamination by a phytoparasitic nematode. The invention, in some aspects includes methods of using phytoparasitic nematode PDE inhibitors to treat a phytoparasitic nematode infection and/or to reduce contamination of a substrate by a phytoparasitic nematode.

Some aspects of the invention include methods such as assays that may be used to identify compounds useful to treat a phytoparasitic nematode infection in a cell or plant, or to reduce or eliminate phytoparasitic nematode contamination of a substrate. Methods of the invention may also be used to determine efficacy, cell toxicity, and other characteristics of PDE compounds that may be used to treat a phytoparasitic nematode infection or to reduce or eliminate phytoparasitic nematode contamination of a substrate.

Phytoparasitic Nematode Infection and Contamination

Phytoparasitic nematodes can infect plants and can also contaminate substrates such as growth media, equipment, soil, etc. Infection of a plant by a phytoparasitic nematode and contamination of a substrate by a phytoparasitic nematode may be characterized by the presence of a life-cycle stage of a phytoparasitic nematode in or on a cell or tissue of the plant and/or in or on the substrate. Phytoparasitic nematodes go through six developmental stages—an egg stage, four immature (juvenile) stages, and an adult stage. Many phytoparasitic nematode species can develop from egg to egg-laying adult in as little as 21 to 28 days under suitable conditions. Phytoparasitic nematodes can survive from season to season primarily as eggs in soil. In the case of root-based phytoparasitic nematodes, after the eggs hatch, the juveniles typically invade roots, usually at root tips, causing some of the root cells to enlarge where the nematodes feed and develop. The male nematodes eventually leave the roots, but the females remain embedded, laying their eggs into a jellylike mass that extends through the root surface and into the soil.

Examples of phytoparasitic nematodes include, but are not limited to: root knot nematodes, stem eelworms and foliar nematodes; *Heterodera* spp., for example, *Heterodera schachtii*, *Heterodora avenae*, *Heterodora trifolii* and *Heterodera glycines*; *Globodera* spp., for example *Globodera rostochiensis*; *Meloidogyne* spp., for example *Meloidogyne incoginita*, *Meloidogyne hapla*, and *Meloidogyne javanica*; *Radopholus* spp., for example *Radopholus similis*; *Pratylenchus*, for example *Pratylenchus neglectans* and *Pratylenchus penetrans*; *Tylenchulus*, for example *Tylenchulus semipenetrans*; *Longidorus*, *Trichodorus*, *Xiphinema*, *Ditylenchus*, *Aphelenchoides* and *Anguina*.

In some embodiments of the invention, PDE inhibitory compounds may be administered to a plant or a substrate to treat a phytoparasitic nematode infection in the plant and to treat the phytoparasitic nematode contamination of the substrate. Thus, the invention in some aspects relates to methods for reducing a phytoparasitic nematode infection or contamination in a plant or in/on a substrate. In some embodiments, reducing a phytoparasitic nematode infection means lowering the amount of a phytoparasitic nematode in or on a plant or in/on a substrate. In some embodiments of the invention, a phytoparasitic nematode infection is reduced by reducing an activity of the phytoparasitic nematode. As used herein, the term "activity" used in reference to a phytoparasitic nematode, may include, but is not limited to phytoparasitic nematode development, hatching, transition from one life-cycle stage to another life-cycle stage, reproduction, replication, chemosensation, chemotaxis, locomotion, invasion of a host, feeding, ingestion, viability, infectivity, establishment of a parasitic interaction with a host, etc. In some embodiments of the invention, reducing an activity of a phytoparasitic nematode includes reducing the viability and/or infectivity of the phytoparasitic nematode. Thus, in certain embodiments of the invention, a phytoparasitic nematode PDE inhibitor compound of the invention may, when contacted with the phytoparasitic nematode, reduce viability and/or infectivity of a phytoparasitic nematode, thus reducing or eliminating a phytoparasitic nematode infection or risk of infection of a plant, and/or reducing or eliminating a phytoparasitic contamination or risk of contamination of a substrate.

In certain embodiments of the invention, methods may include decreasing the number of phytoparasitic nematodes in or on a plant or substrate to a level that is effective to treat the phytoparasitic nematode infection or contamination. As used herein, the terms "treat", "treated", or "treating" when used with respect to a phytoparasitic nematode infection of a plant may refer to a prophylactic treatment that decreases the likelihood of a plant developing the phytoparasitic nematode infection, and also may refer to a treatment after the plant has developed the phytoparasitic nematode infection in order to eliminate or reduce the level of the phytoparasitic nematode infection, prevent the phytoparasitic nematode infection from becoming more advanced (e.g., more severe), and/or slow the progression of the phytoparasitic nematode infection compared to in the absence of the therapy.

As used herein, the terms "treat", "treated", or "treating" when used with respect to a phytoparasitic nematode infection of a plant or contamination in or on a substrate may refer to reducing an activity of an infectious phytoparasitic nematode in or on the plant or substrate. An activity may be reduced by disruption of cyclic nucleotide metabolism in the phytoparasitic nematode. Treating a substrate with a PDE inhibitor compound of the invention may reduce the amount of phytoparasitic nematode in or on the substrate and may also reduce the likelihood of phytoparasitic nematode infection of a plant that contacts the treated substrate. For example, if treatment of a substrate with a PDE inhibitor compound of the invention reduces the amount of infective phytoparasitic nematode on a surface, in soil, etc., the likelihood of infection of a plant that contacts the treated substrate, may be reduced by up 10%, 20%, 30%, 40%, 50%, 60%, 70%, 80%, 90%, 95%, or 100% as compared to the likelihood of phytoparasitic nematode infection of a plant contacted by the untreated substrate. Thus, the treatment of the substrate (e.g., the growth medium, soil, water, etc.) reduces the likelihood of phytoparasitic nematode infection of a plant that contacts the treated substrate.

PDE Inhibitors

Disruption of cyclic nucleotide metabolism in nematodes by inhibiting phosphodiesterase (PDE) activity has been reported to disrupt the life cycle of the roundworm *C. elegans*. It has now been identified that PDEs present in phytoparasitic nematodes have amino acid differences in their PDE inhibitor compound binding sites that can be utilized to selectively target phytoparasitic nematodes to disrupt their life cycle, and to show decreased effect when contacted with non-phytoparasitic nematode PDEs or vertebrate PDEs.

FIG. 1 shows enzymes responsible for regulating levels of cyclic nucleotides in cells. Levels of cyclic nucleotides in cells are controlled by the balance of the rate of synthesis (by adenylate and guanylate cyclases) and degradation (by cyclic nucleotide phosphodiesterases; PDEs). Several classes of phosphodiesterase enzymes exist, with the Class I PDEs being the most common. Class I PDEs are found in all eukaryotes except higher plants.

The vertebrate Class I PDE superfamily consists of 11 distinct enzyme families that share a highly conserved catalytic domain but differ in their substrate specificity, mode of regulation, pharmacological properties, and tissue distribution.

A phylogenetically diverse set of amino acid sequences for the 11 vertebrate PDE sequences has been compiled to generate a representative set of sequences to categorize nematode PDEs. PDE orthologs in selected nematode genomes (*Caenorhabditis* spp. and *M. hapla*) that correspond to vertebrate PDE families 1, 2, 3, 4, 8, and 10, have now been identified. Multiple sequence alignments of the catalytic domain identified 13 unanimous and multiple family-specific sites. For example, analysis of known drug interaction sites of selective inhibitors of human PDE3 and PDE4 showed that ~80% of the residues responsible for drug stabilization in human PDEs are also present in *M. hapla* orthologs, indicating that parasitic nematodes are susceptible to targeted disruption of their life cycle by family-specific PDE inhibitors. Thus, it has now been determined that contacting a phytoparasitic nematode with a phytoparasitic nematode PDE inhibitor can be used to disrupt cyclic nucleotide metabolism in the phytoparasitic nematode, and to inhibit an activity of the phytoparasitic nematode such as replication, viability, infectivity, etc.

As used herein, the term "selective" used in the context of PDE inhibitor families means a PDE inhibitor that reduces PDE activity of members of a PDE family, but does not significantly reduce PDE activity of members of another PDE family. In other words, a selective PDE inhibitor may be a PDE inhibitor that significantly reduces PDE activity of members of a PDE family at a concentration that does not significantly reduce PDE activity of members of another PDE family. For example, under suitable conditions for PDE inhibition, a selective inhibitor of a nematode PDE1 inhibits PDE1 activity but does not inhibit nematode PDE2, PDE3, PDE4, PDE8, or PDE10 activity to a significant extent. Similarly, under suitable conditions for inhibition, a selective inhibitor of vertebrate family PDE10 inhibits PDE10 activity and does not significantly inhibit activity of vertebrate PDE1, PDE2, PDE3, PDE4, PDE5, PDE6, PDE7, PDE8, PDE9, or PDE11. It will be understood that a selective inhibitor of a PDE may inhibit activity of another PDE family, but that it will have significantly lower ability to inhibit that PDE family relative to its ability to inhibit the family for which it is selective.

In some embodiment of the invention, a selective inhibitor may inhibit a level of PDE activity of a different PDE family by an amount that is only up to 5%, 10%, 20%, 30%, 40%, 50%, 60%, 70%, or 80%, of the level of inhibition of a PDE in the family for which the PDE is selective when the activities of the two aforementioned PDEs are compared under similar or identical conditions. Thus, in a non-limiting example, under conditions suitable for PDE inhibition, a selective phytoparasitic nematode PDE1 inhibitor may inhibit none of the activity or up to 1%, 5%, 10%, or 20% of PDE2, PDE3, PDE4, PDE8, or PDE10 activity, but may inhibit (under similar or identical conditions) up to 30%, 40%, 50%, 60%, 70%, 80%, 90%, or 100% of the activity of PDE1. It will be understood that a selective phytoparasitic nematode PDE inhibitor may or may not inhibit a vertebrate and/or non-phytoparasitic nematode PDE ortholog, such as a PDE in a vertebrate or non-phytoparasitic PDE family that corresponds to the PDE phytoparasitic nematode family classification.

Table 1 shows correspondence between vertebrate PDE family members and nematode PDE classifications. An example of an inhibitor that is selective for each vertebrate family is also listed in Table 1. Numerous additional selective inhibitors (e.g., selective for a family/class) are also known in the art [see for example, Bender and Beavo (2006); Lugnier (2006); Francis et al. (2011)].

TABLE 1

| Vertebrate PDE Family | Nematode PDE classification | Example PDE Inhibitor |
|---|---|---|
| PDE1 | PDE-1 | Vinpocetine |
| PDE2 | PDE-2 | EHNA* |
| PDE3 | PDE-3 | Cilostamide |
| PDE4 | PDE-4 | Rolipram |
| PDE10 | PDE-5 | Papaverine |
| PDE8 | PDE-6 | Dipyridamole |

*EHNA = (erythro-9-(2-hydroxy-3-nonyl)adenine

Methods to Identify Candidate Compounds

Certain aspects of the invention include methods of identifying and/or screening additional candidate compounds to identify compounds that may be used to treat a phytoparasitic nematode infection or contamination in a plant or substrate, respectively.

Assay methods of the invention, such as those described in the examples section or others known in the art, may be used to assess the efficacy of PDE compounds to inhibit PDE activity and thereby to reduce phytoparasitic nematode infections and/or contamination of a substrate.

In some aspects of the invention, methods are provided that can be used to identify a phytoparasitic nematode phosphodiesterase (PDE) inhibitor compound, also referred to herein as a "candidate compound" that disrupts cyclic nucleotide metabolism in a phytoparasitic nematode. In some embodiments of the invention the disruption of the cyclic nucleotide metabolism is sufficient to inhibit an activity of the phytoparasitic nematode. Activities, described elsewhere herein, include but are not limited to: viability of the phytoparasitic nematode, infectivity of the phytoparasitic nematode (e.g., the ability of the phytoparasitic nematode to infect a plant), reproducibility or replication of the phytoparasitic nematode, motility of the phytoparasitic nematode, etc. In some embodiments of the invention methods of identifying a phytoparasitic nematode PDE inhibitor compound may include contacting a phytoparasitic nematode test sample with a test compound under conditions suitable for PDE activity; measuring the level of PDE activity in the test sample; comparing the measured level of PDE activity in the test sample to a control level of PDE activity; and determining whether the contacted test sample has a reduced level of PDE activity relative to the control level of PDE activity. A test sample may be a solution of nematodes, nematode cells, disrupted nematode cells, etc., that is suitable for contacting with a candidate PDE inhibitor and determining whether the candidate compound altered, e.g., reduced, the PDE activity in the sample. In some embodiments the determination of a reduced level of PDE activity in the test sample relative to the control level of PDE activity identifies the test compound as a candidate phytoparasitic nematode PDE inhibitor compound that disrupts cyclic nucleotide metabolism in the phytoparasitic nematode. A level of PDE enzymatic activity in a sample can be determined using standard methods known in the art, see for example Zhang et al. (2005).

As described elsewhere herein, various types of control samples can be tested and compared to the effect of contacting a candidate phytoparasitic nematode PDE inhibitor compound with a phytoparasitic nematode. A control sample may be phytoparasitic nematode sample under conditions suitable for PDE activity, (or inhibition of PDE activity) and not contacted with the test compound. In some embodiments of the invention, a control sample may be a vertebrate sample contacted with the candidate compound under suitable conditions for PDE activity (or inhibition of PDE activity) in the vertebrate sample, or a control sample may be a non-phytoparasitic nematode sample contacted with the candidate compound under suitable conditions for PDE activity (or inhibition of PDE activity) in the non-phytoparasitic nematode sample.

In certain embodiments, a determination that PDE activity is reduced in a phytoparasitic nematode test sample relative to a vertebrate or non-phytoparasitic nematode control sample identifies the test compound as specifically disrupting cyclic nucleotide metabolism in the phytoparasitic nematode compared to the vertebrate, or the non-phytoparasitic nematode, respectively. A PDE inhibitor compound that is specific for a phytoparasitic nematode PDE compared to a vertebrate or non-phytoparasitic nematode PDE is an inhibitor compound that has a higher relative level of inhibition in a phytoparasitic nematode then of a vertebrate or non-phytoparasitic nematode. In some embodiments, such a specific PDE inhibitor may be desirable for treatment of a phytoparasitic nematode infection or contamination because it is less likely than a less specific PDE inhibitor to be toxic or harmful to a vertebrate or non-phytoparasitic nematode when used in a treatment against or for decontamination against a phytoparasitic nematode.

In some embodiments, methods of the invention for identifying a candidate compound may utilize control samples that comprise a vertebrate PDE that is an ortholog to a phytoparasitic nematode PDE. Similarly, in some embodiments of the invention, a control sample may comprise a non-phytoparasitic nematode PDE that is an ortholog to a phytoparasitic nematode PDE.

A test compound to assay using a method of the invention can be selected for one or more reasons or characteristics. Test compounds may be obtained from a library or other collection of potential test compounds. In some embodiments of the invention, a test compound may have a particular structure feature, sequence characteristic, binding characteristic, or functionality. For example, in some embodiments of the invention, a test compound is a compound that selectively binds a catalytic binding site of a phytoparasitic nematode PDE as compared to the binding of the test compound to a corresponding catalytic binding site of a non-phytoparasitic nematode PDE ortholog and/or a vertebrate PDE ortholog. As another example, the affinity of a PDE inhibitor to the phytoparasitic nematode PDE can be greater than the affinity of the PDE inhibitor to a control PDE such as a non-phytoparasitic nematode PDE or a vertebrate PDE. Affinity of a PDE inhibitor to a PDE can be determined using standard methods to assess binding characteristics and binding coefficients. In another example, one or more differences between the amino acid sequence of a catalytic domain of a phytoparasitic nematode PDE and a sequence of a corresponding catalytic domain of a non-phytoparasitic nematode PDE ortholog or a vertebrate PDE ortholog can be compared and PDE inhibitor test compounds may be selected for testing and assays of the invention based at least in part on the one or more identified differences between the catalytic domain sequences. See Examples section and FIG. 4 for differences in residues in amino acid sequences that may be utilized in the determination of PDE inhibitors that are more specific for phytoparasitic nematode PDEs than for vertebrate and/or non-phytoparasitic nematode PDEs, for use in methods of the invention.

Some embodiments of the invention include methods of assessing efficacy of a compound for the treatment of a phytoparasitic nematode infection or contamination by a phytoparasitic nematode. The invention, in some aspects may include contacting an identified PDE inhibitor test or candidate compound with a phytoparasitic nematode and testing to see the effect on an activity of the phytoparasitic nematode. Examples of testing means that may be used include but are not limited to, determining whether the compound modifies PDE activity in the phytoparasitic nematode, determining whether the compound reduces a phytoparasitic nematode activity such as replication, infectivity, viability, etc. Non-limiting examples of assays that may be used for testing are set forth in the Examples, and other art-known assays. Methods can be used that permit assessment of phytoparasitic nematode infection and/or contamination before and after contact with the compound, which may also be referred to herein as a test or candidate compound or agent. A decrease in the amount of an activity of the phytoparasitic nematode and/or the amount of the phytoparasitic nematode in comparison to a suitable control is indicative of a compound agent capable of treating a phytoparasitic nematode infection or contamination. In certain embodiments of the invention, efficacy of a PDE inhibitor can be determined by assessing enzyme activity, a downstream effect of enzyme activity, etc. Means for such assessment of PDE inhibitor effectiveness and efficacy are known in the art.

An assay mixture useful to assess a treatment candidate for a phytoparasitic nematode infection comprises a test PDE inhibitor compound. The candidate compound may be an antibody, small organic compound, small molecule, polypeptide, nucleic acid, etc., and accordingly can be selected from combinatorial antibody libraries, combinatorial protein libraries, small organic molecule libraries, or any other suitable source. Typically, a plurality of reaction mixtures is run in parallel with different test PDE inhibitor compound concentrations to obtain a different response to the various concentrations. Typically, one of these concentrations serves as a negative control, i.e., at zero concentration of the candidate compound or at a concentration of compound below the limits of assay detection.

Test compounds may be obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random or non-random polypeptides, combinatorial libraries of proteins or antibodies, and the like. Alternatively, libraries of natural compounds in the form of bacterial, fungal, plant, and animal extracts are available or readily produced. Additionally, natural and synthetically produced libraries and compounds can be readily be modified through conventional chemical, physical, and biochemical means. Further, known compounds, which may be USDA approved compounds to treat other diseases or conditions in plants, may be subjected to directed or random chemical modifications such as acylation, alkylation, esterification, amidification, etc. to produce structural analogs of the compounds.

Non-limiting examples of assays and methods to test a candidate compound, identify a compound that may treat a phytoparasitic nematode infection or contamination, and to assess efficacy of compounds such as assays of phytoparasitic nematode number and/or one or more phytoparasitic nematode activities are provided herein in the Examples section.

Methods and Compounds to Reduce Phytoparasitic Nematode Activity

A number of treatment methods and compounds of the invention have been identified as useful to treat infection and/or contamination by phytoparasitic nematode species. Methods of the invention that relate to anti-phytoparasitic nematode activity include treatment of phytoparasitic nematode in plants, including, but not limited to agricultural crop plants. Thus, compounds and methods of the invention may be used to treat phytoparasitic nematode infections in plants, and may also be administered to decontaminate phytoparasitic nematode contamination of a substrate. It has now been identified that PDE inhibitor compounds can be used, independent of any prior known use, to reduce one or more phytoparasitic nematode activity and treat a phytoparasitic nematode infection in a plant.

Phosphodiesterase (PDE) inhibiting compounds have now been identified as useful to treat phytoparasitic nematode infections and contamination. As used herein, a PDE inhibiting compound means a compound that reduces or eliminates PDE activity in a contacted cell or organism, for example in a phytoparasitic nematode contacted with the compound. The term "anti-phytoparasitic nematode agent" is also used herein to refer to a compound that may be used to treat a phytoparasitic nematode infection, reduce contamination of a substrate by a phytoparasitic nematode, and/or to inhibit one or more activities of a phytoparasitic nematode. A non-limiting example of an anti-phytoparasitic nematode agent is a phosphodiesterase (PDE) inhibitor.

A treatment method of the invention may include contacting a phytoparasitic nematode with an amount of a phytoparasitic nematode PDE inhibitor in an amount that is effective to reduce one or more activities of the phytoparasitic nematode. In some embodiments of the invention, contacting a phytoparasitic nematode with a PDE inhibitor reduces the level of one or more activities of the phytoparasitic nematode by at least 10%, 15%, 20%, 25%, 30%, 35%, 40%, 45%, 50%, 55%, 60%, 65%, 70%, 75%, 80%, 85%, 90%, 95%, or 100% compared to a control level of activity in a phytoparasitic nematode not contacted with the PDE inhibitor. In certain embodiments, the level of one or more activities of the phytoparasitic nematode is reduced by at least 20%, 30%, 40%, or 50% compared to a control level of activity in a phytoparasitic nematode not contacted with the PDE inhibitor.

In some embodiments of the invention, a treatment method includes contacting a phytoparasitic nematode, under conditions suitable for PDE inhibition, with a phytoparasitic nematode PDE inhibitor compound that has little or no negative effect of a biological function of a vertebrate or non-phytoparasitic organism with which it contacts. Thus, in some embodiments of the invention a phytoparasitic nematode PDE inhibitor has little or no toxicity when contacted with a vertebrate organism or non-phytoparasitic nematode in the course of its use in treating a phytoparasitic nematode infection or contamination. One of ordinary skill will recognize that conditions suitable for PDE inhibition in a sample, are conditions under which PDE activity can occur and/or is occurring. For example, though not intended to be limiting, a sample may be one in which PDE activity is occurring or is induced to occur. Thus PDE activity can be detected in a sample not contacted with a PDE inhibitor, and it can be determined whether contacting the sample with a PDE inhibitor compound reduces PDE activity. Conditions suitable for PDE inhibition may be physiological conditions normal for the organism whose PDE activity is being investigated. It will be understood that PDE inhibition may be determined or measured using art-known methods, including detection of the enzyme's activity, determination of a downstream effect of the enzyme's activity, etc. In some embodiments, suitable conditions may include use of (for example, contact with) equivalent inhibitor concentrations for the phytoparasitic nematode PDE inhibitor compound, the vertebrate PDE inhibitor compound, and/or the non-phytoparasitic nematode inhibitor compound.

In some embodiments of the invention, a test compound can be contacted with a sample under conditions suitable for PDE activity in the sample, and if the PDE activity in the sample is reduced or inhibited compared to a similar sample not contacted with the test compound, it indicates the test compound is a candidate PDE inhibitor compound. As used herein the term "suitable for PDE activity" means conditions under which a PDE functions. For example, temperature, assay components, physiological parameters, etc., under which PDE activity occurs in a sample, for example, physiological conditions normal for the organism whose PDE activity is being investigated. Art-known conditions suitable for PDE activity may be used in assays and methods of the invention.

In some embodiments of the invention, contacting a vertebrate or non-phytoparasitic nematode sample (e.g., a control sample) with a phytoparasitic nematode PDE inhibitor under conditions suitable for PDE inhibition in the vertebrate or non-phytoparasitic nematode sample, respectively, does not result in a significant level of PDE inhibition in the vertebrate or non-phytoparasitic nematode sample. As used herein, the phrase "does not result in a significant level" used in relation to the effects of a PDE inhibitor means that although contact with the PDE inhibitor may result in some PDE inhibition, the level of inhibition does not result in statistically significant toxicity or negative effect on a biological function of the vertebrate or non-phytoparasitic nematode sample.

In certain embodiments, contacting a vertebrate sample (e.g., a control sample) with a phytoparasitic nematode PDE inhibitor under conditions suitable for PDE inhibition in the vertebrate sample does not result in a statistically significant negative effect on a biological function of the vertebrate sample.

In some embodiments of the invention, contacting a vertebrate sample (e.g., a control sample) with a phytoparasitic nematode PDE inhibitor compound under conditions suitable for PDE inhibition in the vertebrate sample does not result in a significant level of PDE inhibition in the vertebrate sample. The level of PDE inhibition in the vertebrate sample may be zero or for example, less than 20% or 30% inhibition of the level of PDE activity in the vertebrate sample not contacted with the phytoparasitic nematode PDE inhibitor compound. Similarly, contact of a vertebrate sample does not result in significant toxicity or negative effect on a biological function of the vertebrate cell, tissue or organism of the sample. Art-known tests for toxicity and/or biological functions can be used to assess the effects of PDE inhibitor compounds of the invention.

In certain embodiments of the invention, a phytoparasitic nematode PDE inhibitor is a PDE inhibitor compound that is more effective at inhibiting a phytoparasitic nematode PDE than at inhibiting a vertebrate ortholog PDE. Thus, under suitable conditions for PDE inhibition, a phytoparasitic nematode PDE inhibitor may have a higher level of inhibitory activity against the phytoparasitic nematode PDE than against the vertebrate PDE ortholog. In some embodiments of the invention, contacting a vertebrate PDE ortholog with a phytoparasitic nematode PDE inhibitor under suitable conditions for PDE inhibition, results in a level of inhibition of the vertebrate PDE ortholog that is zero, and/or less than 20%, 30%, 40%, or 50%, of the level of inhibition of the phytoparasitic nematode PDE contacted by the selective phytoparasitic nematode PDE inhibitor under suitable conditions (which may in some embodiments, include equivalent inhibitor concentrations) for PDE inhibition.

In certain embodiments, contacting a non-phytoparasitic nematode sample (e.g., a control sample) with a phytoparasitic nematode PDE inhibitor under conditions suitable for PDE inhibition in the non-phytoparasitic nematode sample does not result in a statistically significant toxicity or negative effect on a biological function of the non-phytoparasitic nematode sample. In some embodiments of the invention, contacting a non-phytoparasitic nematode sample (e.g., a control sample) with a phytoparasitic nematode PDE inhibitor compound under conditions suitable for PDE inhibition in the non-phytoparasitic nematode sample does not result in a significant level of PDE inhibition in the non-phytoparasitic nematode sample. The level of PDE inhibition in the vertebrate sample may be zero and/or may be less than for example, 20% or 30% of the inhibition of the level of PDE activity in the non-phytoparasitic nematode sample not contacted with the phytoparasitic nematode PDE inhibitor compound. Similarly, contact of a non-phytoparasitic nematode sample does not result in significant toxicity or negative effect on a biological function of the non-phytoparasitic nematode cell, tissue or organism of the sample. Art-known tests for toxicity and/or biological functions can be used to assess the effects of PDE inhibitor compounds of the invention.

In certain embodiments of the invention, a phytoparasitic nematode PDE inhibitor is a PDE inhibitor compound that is more effective at inhibiting a phytoparasitic nematode PDE than inhibiting a non-phytoparasitic nematode ortholog PDE. Thus, under suitable conditions for PDE inhibition, a phytoparasitic nematode PDE inhibitor may have a higher level of inhibitory activity against the phytoparasitic nematode PDE than against the non-phytoparasitic nematode PDE ortholog. In some embodiments of the invention, contacting a non-phytoparasitic nematode PDE ortholog with a phytoparasitic nematode PDE inhibitor under suitable conditions for PDE inhibition, results in a level of inhibition of the non-phytoparasitic nematode PDE ortholog that is up to zero, and/or less than 20%, 30%, 40%, 50%, 60%, 70%, 80%, 90%, 99%, or 100% of the level of inhibition of the phytoparasitic nematode PDE contacted by the selective phytoparasitic nematode PDE inhibitor under suitable conditions (which may in some embodiments, include equivalent inhibitor concentrations) for PDE inhibition. In some embodiments of methods of the invention, the non-phytoparasitic nematode is *C. elegans*.

Samples and Controls

As used herein with reference to testing and assays, a "sample" may comprise one or more eggs, cells, cell components, disrupted cells, tissues, or organisms. In some embodiments, a sample may comprises one or more phytoparasitic nematodes; one or more phytoparasitic nematode cells; a phytoparasitic nematode tissue; one or more non-phytoparasitic nematodes; one or more non-phytoparasitic nematode cells; a non-phytoparasitic nematode tissue; one or more vertebrate cells; a vertebrate tissue or organism; one or more plant cells; a plant tissue or entire plant, including but not limited to a stem, leaf, root, etc. A sample may be an in vitro sample or an in vivo sample. Eggs, cells, tissues, organisms may be in culture and may be isolated from their site of origin.

There are varied life stages of phytoparasitic nematodes. In some embodiments of the invention, the stage of a phytoparasitic nematode is in an egg or embryonic stage. In certain embodiments of the invention, the stage of a phytoparasitic nematode is a more mature stage. Some infections or contaminations by phytoparasitic nematodes that can be treated using methods and compounds of the invention may be characterized by the presence of phytoparasitic nematodes in an egg or embryonic stage and some may be characterized by the presence of phytoparasitic nematodes in a juvenile or adult stage.

A level or presence of a phytoparasitic nematode infection, or the level or presence of contamination of a substrate by a phytoparasitic nematode can be determined and compared to control values to assess efficacy of a treatment of the invention. For example, the level, amount, or activity of a phytoparasitic nematode found in cells, tissues, plants that do not have a phytoparasitic nematode infection can be compared to the levels, amounts, or activity in a treated cell, tissue, or plant to determine efficacy of a compound and treatment of the invention. Similarly, control values such as a level or activity of phytoparasitic nematode on a substrate, or the infectivity of a contaminated substrate can be compared with levels and infectivity following treatment with a compound of the invention as a measure of the effectiveness of the compound and/or treatment.

In some aspects of the invention, a control value may be a PDE activity value or level determined in a phytoparasitic nematode sample under conditions suitable for PDE activity when the PDE is not contacted with a PDE inhibitor test compound. Comparing results of such a control with a level of PDE activity determined in a phytoparasitic nematode sample under the same conditions but included contact with the test compound, permits determination of whether or not the test compound has an effect on PDE activity.

In some aspects of the invention a control sample may be a non-phytoparasitic nematode sample, and may be used to compare the effect of a PDE inhibitor test compound on activity of a phytoparasitic nematode PDE with the effect of the PDE inhibitor test compound on activity of a non-phytoparasitic nematode PDE. Thus, in some embodiments of the invention, a control sample may be a non-phytoparasitic nematode sample, and include for example, a non-phytoparasitic nematode cell, tissue or organism that is contacted with a PDE inhibitor candidate compound under suitable conditions for PDE activity to occur in the non-phytoparasitic nematode sample. The level of PDE activity, which may be used to determine a level of PDE inhibition by the compound, can be compared to the level of PDE activity in a phytoparasitic nematode test sample that is contacted with the PDE inhibitor candidate compound under suitable conditions for PDE activity. In some embodiments of the invention, a reduction in PDE activity in the phytoparasitic nematode test sample relative to the non-phytoparasitic nematode control sample indicates that the PDE inhibitor compound is more effective at inhibiting the phytoparasitic nematode PDE than at inhibiting the non-phytoparasitic nematode PDE. Such a result identifies the PDE inhibitor test compound as selective for, (for example, more effective at inhibiting) the phytoparasitic nematode PDE compared to its effectiveness at inhibiting the non-phytoparasitic nematode PDE. A PDE inhibitor that more effectively inhibits a phytoparasitic nematode PDE than a non-phytoparasitic nematode PDE may be considered to be selective for disrupting cyclic nucleotide metabolism in the phytoparasitic nematode compared to the vertebrate. In some embodiments, the non-phytoparasitic nematode PDE is an ortholog of the phytoparasitic nematode PDE.

In some aspects of the invention a control sample may be a vertebrate sample, and may be used to compare the effect of a PDE inhibitor test compound on activity of a phytoparasitic nematode PDE with the effect of the PDE inhibitor test compound on activity of a vertebrate PDE. Thus, in some embodiments, a control sample may be a vertebrate sample, and include for example, a vertebrate cell, tissue, or organism that is contacted with a PDE inhibitor candidate compound under suitable conditions for PDE activity to occur in the vertebrate sample. The level of PDE activity, which may be used to determine a level of PDE inhibition by the compound, can be compared to the level of PDE activity in a phytoparasitic nematode test sample that is contacted with the PDE inhibitor candidate compound under suitable conditions for PDE activity. In some embodiments of the invention, a reduction in PDE activity in the phytoparasitic nematode test sample relative to the vertebrate control sample indicates that the PDE inhibitor compound is more effective at inhibiting the phytoparasitic nematode PDE than at inhibiting the vertebrate PDE. Such a result identifies the PDE inhibitor test compound as selective for, (for example, more effective at inhibiting) the phytoparasitic nematode PDE compared to its effectiveness at inhibiting the vertebrate PDE. A PDE inhibitor that more effectively inhibits a phytoparasitic nematode PDE than a vertebrate PDE may be considered to be selective for disrupting cyclic nucleotide metabolism in the phytoparasitic nematode compared to the vertebrate. In some embodiments, the vertebrate PDE is an ortholog of the phytoparasitic nematode PDE.

A control value may be a predetermined value, which can take a variety of forms. It can be a single cut-off value, such as a median or mean. It can be established based upon comparative groups, such as in groups not having a phytoparasitic nematode infection or phytoparasitic nematode contamination and groups having a phytoparasitic nematode infection or phytoparasitic nematode contamination. Another example of comparative groups may be groups having one or more symptoms of, or a diagnosis of, a phytoparasitic nematode infection, and groups without having one or more symptoms of or a diagnosis of the phytoparasitic nematode infection. Another comparative group may be a plurality of plants with a history of a phytoparasitic nematode infection and a group without such a history. A predetermined value can be arranged, for example, where a tested population is divided equally (or unequally) into groups, such as a low-risk group, a medium-risk group and a high-risk group or into quadrants or quintiles, the lowest quadrant or quintile being plants or plurality of plants with the lowest risk (for example of a phytoparasitic nematode infection) and the lowest level of phytoparasitic nematode, or phytoparasitic nematode activity and the highest quadrant or quintile being plants or plurality of plants with the highest risk (for example of a phytoparasitic nematode infection) and highest levels of phytoparasitic nematodes or phytoparasitic nematode activity.

The predetermined value, of course, will depend upon the particular population selected. For example, an apparently healthy population of plants will have a different "normal" range than will a population of plants that is known to have a phytoparasitic nematode infection or presence. Accordingly, the predetermined value selected may take into account the category in which an individual plant, plurality of plants, or cells fall. Appropriate ranges and categories can be selected with no more than routine experimentation by those of ordinary skill in the art. As used herein, "abnormal" means significantly different as compared to a normal control. By abnormally high levels of a phytoparasitic nematode (which may indicate a phytoparasitic nematode infection and/or a phytoparasitic nematode contamination) it is meant high relative to a selected control, and may include a statistically significant increase in a phytoparasitic nematode level. In some embodiments, a statistically significant increase may be an activity increase of at least up to 5%, 10%, 20%, 30%, 40%, 50%, 60%, 70%, 80%, 90%, 100%, 150%, 200%, or more, in a plant, plurality of plants, cell, tissue, or substrate as compared to the level in a normal control. It will be understood that a control may have zero phytoparasitic nematodes and that any level higher than such a control may indicate the presence of a phytoparasitic nematode infection or contamination as compared to that control.

Treatment with a compound of the invention, may result in a reduction in the level or activity of a phytoparasitic nematode compared to an abnormal control (e.g., a level that indicates infection or contamination) and include a statistically significant decrease in activity. In some embodiments, a statistically significant decrease may be an activity decrease of at least up to 5%, 10%, 20%, 30%, 40%, 50%, 60%, 70%, 80%, 90%, or 100% in a plant, plurality of plants, cell, tissue, or substrate as compared to the level in a normal control, and may be a decrease of up to 5%, 10%, 20%, 30%, 40%, 50%, 60%, 70%, 80%, 90%, 100% of the level or activity of a phytoparasitic nematode in a plant, plurality of plants, cell, tissue, or surface as compared to the level in the abnormal control. Typically, a normal control will be based on apparently healthy normal plants or pluralities of plants in an appropriate developmental stage or apparently healthy cells and tissues; and an abnormal control will be based on plants or plurality of plants that have a phytoparasitic nematode infection and/or substrates known to be contaminated with the phytoparasitic nematode.

In some aspects of the invention, levels of a phytoparasitic nematode and/or of an activity of a phytoparasitic nematode may be determined for a plant or plurality of plants may serve as control values for later determinations of the phytoparasitic nematode in that same plant or plurality of plants, thus permitting assessment of changes from a "baseline" phytoparasitic nematode infection in a plant or across a plurality of plants. Thus, an initial level of phytoparasitic nematode and/or a phytoparasitic nematode activity may be determined in a plant or plurality of plants on/in a substrate and methods and compounds of the invention may be used to decrease the level of the phytoparasitic nematode and/or phytoparasitic nematode activity in the plant or plurality of plants or in/on the substrate, with the initial level serving as a control level for that subject or substrate, respectively. Using methods and compounds of the invention, the level of a phytoparasitic nematode and/or an activity of a phytoparasitic nematode in the plant or plurality of plants or on the substrate may be decreased by up to 5%, 10%, 20%, 30%, 40%, 50%, 60%, 70%, 80%, 90%, 95%, or 100%, compared to the initial level, by administering a treatment for the phytoparasitic nematode infection to the plant or plurality of plants or in/on the substrate, respectively.

It will be understood that controls according to the invention may be, in addition to predetermined values, samples of materials tested in parallel with the experimental materials. Examples include samples from control populations or control samples generated through manufacture to be tested in parallel with the experimental samples.

Treatment of Plants

In some aspects of the invention treatment of a phytoparasitic nematode infection may be performed with methods that include contacting a plant with a PDE-inhibitor compound and in certain embodiments, treatment of a phytoparasitic nematode infection may be performed with methods that include contacting the environment of a plant with a PDE-inhibitor compound and having the phytoparasitic nematode infection treated in the environment. In some embodiments, the environment of a plant shall be understood to include the growth medium of the plant, which may include, but is not limited to soil, water, fertilizer, manure, peat, loam, vermiculite, an agricultural medium, an aqueous growth medium, or a planting medium.

A phytoparasitic nematode infection in a plant may be characterized by the presence of one or more phytoparasitic nematodes in or on the plant. As used herein, a plant shall mean a plant that is susceptible to infection by a phytoparasitic nematode including but not limited to agricultural crop plants. Examples of plants susceptible to infection by a phytoparasitic nematode may include, but are not limited to: fruit-bearing plants, trees, grasses, monocots, dicots, vegetable plants, and non-fruit bearing plants. Examples of plants that are susceptible to phytoparasitic nematode infection and may be treated with methods and compounds of the invention include, but are not limited to: *capsicum*, chili, radishes, bananas, grapes, passionfruit, pineapples, pawpaw, cotton, albezia, alder, azalea, boxwood, cactus, *catalpa*, cedar, *euonymus*, fir, ginkgo, hibiscus, *hydrangea*, juniper, larch, lilac, mulberry, oak, palm, pine, *pittosporum*, poinsettia, rose, spruce, tamarisk, grape, blackberry/raspberry, strawberry, almond, apple, apricot, avocado, cherry, citrus, olive, peach/nectarine, pear, plum/prune, walnut, beans, beets, carrots, celery, cole crops, corn (maize), cucumbers, eggplant, garlic, lettuce, melons, onions, peas, peppers, potatoes (Irish), potatoes (sweet), radish, spinach, squash, soybeans, tomatoes, turnips, and pumpkins.

Thus, the invention can be used to treat phytoparasitic nematode infections of numerous plant varieties. For instance, methods and compositions of the invention can be used in professional agricultural applications as well as in amateur gardening applications. In some embodiments of the invention, the term "subject" refers to is a plant. In some embodiments of the invention, a plant treated with a method of the invention does not have a condition, infection, or contamination that would otherwise be treated by the compound of the invention that is administered to the plant to treat the phytoparasitic nematode infection. In certain embodiments of the invention, a subject does not have an infestation or infection by an insect, including but not limited to an infestation and/or infection by a moth, grasshopper, meal worm, etc.

Non-limiting examples of subjects to which the present methods and compounds of the invention can be applied are plants that are known to have, suspected of having, or at risk of having, a phytoparasitic nematode infection. Methods of the invention may be applied to a plant that at the time of treatment, has been confirmed to have a phytoparasitic nematode infection, or a plant that is considered to be at risk for having or developing a phytoparasitic nematode infection. Identification of a phytoparasitic nematode infection in a plant may be done using art-known assays and/or through observations of plant health and vitality. For examples, samples may be obtained from a plant or plurality of plants and assessed for the presence of one or more phytoparasitic nematodes. In some embodiments a sample is tested for the presence of an embryonic-stage nematode, (e.g., egg stage), a juvenile-stage nematode, or an adult-stage nematode. The presence of one or more of the life-cycle stages of a phytoparasitic nematode in or on a plant may indicate infection of the plant. The presence of one or more of the life-cycle stages of a phytoparasitic nematode in the immediate environment of a plant, for example the soil in which the plant is grown, or a neighboring plant, may indicate a risk of infection of the plant.

In some aspects of the invention, a plant that has phytoparasitic nematode infection may be a plant that displays sufficient symptoms of the infection to be considered suitable for treatment with a compound of the invention, or may be a plant that has been identified and confirmed to have the infection. Examples of symptoms that may indicate a phytoparasitic nematode infection are known by those of skill in the art, and may include, but are not limited to loss of leaf matter, yellowing, presence of root galls, leaf wilting, stem wilting, nutritional deficits, stunted growth, plant death, etc.

In some aspects of the invention, a plant is at risk of having or developing a phytoparasitic nematode infection. A plant at risk of developing a phytoparasitic nematode is one that has an increased probability of developing the phytoparasitic nematode infection, compared to a control risk of developing the phytoparasitic nematode infection. In some embodiments of the invention, a level of risk may be statistically significant compared to a control level of risk. A plant at risk may, for instance, be a plant in a geographic location known to put plants at risk of phytoparasitic nematode infection; a plant in proximity of other plants known to have a phytoparasitic nematode infection; a seed or seedling of a plant that may have been exposed to a phytoparasitic nematode infection at a pre-planting stage, and/or a plant that has previously been treated for the phytoparasitic nematode infection and that may be considered to be at risk for recurrence or a chronic phytoparasitic nematode infection.

In some embodiments of the invention, a treatment of a plant is a prophylactic treatment and in certain embodiments, a plant is selected for treatment with a compound of the invention at least in part on the basis that the plant has been, or may have been exposed to a phytoparasitic nematode infection. In some embodiments of the invention, the plant that is treated using a compound of the invention has been diagnosed with a phytoparasitic nematode infection.

As used herein a cell, tissue or plant or portion of a plant that may be contacted and treated with a method or compound of the invention may be at a developmental stage including, but not limited to: an un-germinated seed, a germinated seed, a plantlet, a seedling, an adult plant, or a portion of a plant such as a fruit, vegetable, leaf, stem, flower, root, root hair, etc.

Some embodiments of the invention include methods of administering a PDE inhibitor compound to a plant or portion of a plant in an amount effective to inhibit one or more phytoparasitic nematode activities in the plant as a treatment for the phytoparasitic nematode infection of the plant and or phytoparasitic nematode contamination of the substrate.

Treating Environment of Plant

In addition to the use of compounds and methods of the invention to treat phytoparasitic nematode infections in plants, compounds and methods of the invention may be used to treat (e.g., decontaminate) the environment of a plant, or other substrate that may include one or more phytoparasitic nematodes. As used herein, the "environment" of a plant means substrates that are in physical association with the plant, in contact with the plant, in reasonable proximity to the plant, etc. Thus, methods to reduce or eliminate phytoparasitic nematode contamination in a substrate are also useful to reduce or eliminate phytoparasitic nematode contamination in the environment of a plant. It is understood that phytoparasitic nematode eggs or other life-cycle stages may be found an environment of a plant, such as in growth medium, soil, or another substrate. Compounds and methods of the invention may be used to decontaminate substrates that include a phytoparasitic nematode. Examples of substrates that may be treated with a compound and/or method of the invention to reduce or eliminated phytoparasitic nematode contamination may include, but are not limited to: plant growth medium, plant storage or transport media, soil, water, fertilizer, manure, peat, loam, mulch, vermiculite, agricultural media, aqueous growth media, planting media, rooting media, plant pot, plant container, tools, agricultural equipment, gardening equipment, etc.

Application/Administration to Plants and Plant Environment

A variety of routes are available to administer a PDE inhibitor compound of the invention to a plant and/or to the environment of the plant. The particular delivery mode selected will depend, of course, upon the stage of the plant, the plant location, the phytoparasitic nematode infection being treated, and the dosage required for efficacy at reducing one or more PDE activities in the plant. In some embodiments of the invention, a PDE inhibitor compound of the invention is administered to a plant by contacting a plant surface with the PDE inhibitor compound. Means of application or administration of nematicides are well known in the art, and may include contacting the plant with the PDE inhibitor compound by spraying, dipping, dusting at least a portion of the plant with a composition that includes the PDE inhibitor compound. Additional means of application or administration may include providing a solution, such as an aqueous solution, that comprises one or more phytoparasitic nematode PDE inhibitor compounds. The aqueous solution can be taken up via a plant leaf, root, etc. and thus used to deliver the phytoparasitic nematode PDE inhibitor compound into the plant where it contacts a phytoparasitic nematode and reduces one or more activities of the phytoparasitic nematode. Another example of a means of delivering a phytoparasitic nematode PDE inhibitor compound into a plant may include placing a phytoparasitic nematode PDE inhibiting compound within a slow release matrix and administered by placement of the matrix in reasonable proximity to the plant to permit the phytoparasitic nematode PDE inhibitor compound to be taken up by the plant in an amount effective to reduce one or more activities of a phytoparasitic nematode in or on the plant. In some embodiments of the invention, administration of a phytoparasitic nematode PDE inhibitor is a prophylactic administration.

Decontamination Treatments for Substrates

As described elsewhere herein, methods of the invention may include contacting a substrate with a phytoparasitic nematode PDE inhibitor compound of the invention to decrease or eliminate the contamination by the phytoparasitic nematode. Thus, in some embodiments, methods of the invention include decontaminating a substrate that has phytoparasitic nematode contamination or is at risk of having phytoparasitic nematode contamination. In some embodiments, the methods include contacting the substrate with an effective amount of at least one phytoparasitic nematode PDE inhibitor compound of the invention. The substrate is contacted with an effective amount of the phytoparasitic nematode PDE inhibitor compound to reduce the phytoparasitic nematode contamination of or the risk of phytoparasitic nematode contamination of the substrate. As described herein, the contamination may be due to the presence of one or more species of phytoparasitic nematode.

Reduction in the phytoparasitic nematode contamination of a substrate may include a reduction in the amount or activity of the phytoparasitic nematode in or on the substrate. Such a reduction may result in the substrate being less "infectious" when contacted by a plant. In some embodiments of the invention the efficacy of a treatment to decontaminate a substrate may be determined by measuring and assessing the amount of phytoparasitic nematodes in or on the substrate following contact with a PDE inhibiting compound of the invention. In certain embodiments of the invention the efficacy of a treatment to decontaminate a substrate may be determined by measuring and assessing the infectivity of the substrate when contacted by a plant after treatment of the substrate compared to infectivity of an untreated substrate (e.g., a control, untreated substrate). Less infections may mean less likely to be infect a plant, which may be up to 20%, 30%, 40%, 50%, 60%, 70%, 80%, 90%, or 100% less likely to be infected than if contacted by an untreated substrate.

The term "substrate" as used in reference to compounds and treatments of the invention, includes any type of material that may be contaminated by a phytoparasitic nematode. In some embodiments of the invention, a substrate is a plant growth medium, plant storage or transport media, soil, water, fertilizer, manure, peat, loam, mulch, vermiculite, agricultural media, aqueous growth media, planting media, rooting media, plant pot, plant container, tools, agricultural equipment, gardening equipment, etc.

A contaminated substrate that can be decontaminated using a method and/or compound of the invention may have one or more phytoparasitic nematodes in or on the substrate. A phytoparasitic nematode that contaminates a substrate may be a nematode egg, e.g., an embryonic-stage nematode; or may be a juvenile-stage nematode or an adult-stage nematode. In certain embodiments of the invention a contaminated substrate includes contamination by more than one stage of phytoparasitic nematodes.

Application/Administration to Substrates

A PDE inhibitor compound of the invention may be contacted with a substrate using any suitable means. In some embodiments of treatment methods of the invention the contaminated substrate is contacted with an aqueous composition comprising the compound of the invention. The aqueous composition may also include a colorant, scent, carrier, or other component that is suitable for delivery of a compound of the invention to a potentially contaminated substrate. A compound of the invention can be delivered to a substrate via any suitable process, including, but not limited to, spraying, or wiping, coating, dusting, sprinkling, etc., the substrate with a mixture or solution that contains the phytoparasitic nematodes PDE inhibitor compound of the invention. Additional means of contacting a substrate with a PDE inhibitor compound of the invention may include dipping, immersion, etc. of the substrate into a solution that contains the compound. In addition, some substrates such as dirt, vermiculite, manure, soil, potting medium, water, etc. may have a PDE inhibitor compound of the invention added to the substrate directly, by pouring, mixing etc. of a dry mixture or wet solution that contains the PDE inhibitor compound into the substrate. In some embodiments of the invention, a compound of the invention is part of a composition that is contacted with a substrate to treat a phytoparasitic nematodes infection. In some embodiments of the invention such a composition may be non-sterile and in certain embodiments of the invention the composition may be sterile.

Phytoparasitic Nematode PDE Inhibitor Compounds

Compounds of the invention may be administered to a cell, tissue, or plant in the form of a nematicide. A nematicide of the invention may be manufactured for the treatment of a phytoparasitic nematode infection. As used herein the terms "nematicide agent" and "anti-phytoparasitic-nematode agent" may be used interchangeably, and refer to a compound that is when contacted with a cell, plant, nematode, or substrate acts to reduce an infection or reduce contamination by a phytoparasitic nematode. Thus, compounds of the invention useful to treat a phytoparasitic nematode infection or contamination may be referred to as nematicide agents or anti-phytoparasitic nematode agents. Additional compounds that are anti-phytoparasitic nematode agents or phytoparasitic nematicide agents are known in the art and include, but are not limited to pesticide fumigant or a compound that stimulates synthesis of cyclic nucleotides.

Compounds of the invention may be administered singly or in combination with one or more additional compounds or agents. In some embodiments, a compound of the invention may act in a synergistic manner with one or more other anti-phytoparasitic nematode agents or treatments and increase the effectiveness of the one or more anti-phytoparasitic nematode agents or activities. Thus, for example, administration or application of a phytoparasitic nematode PDE inhibitor compound that reduces one or more phytoparasitic nematode activities such as, but not limited to replication, viability, infectivity, etc., may be administered or applied to a plant or substrate with another compound that treats the phytoparasitic nematode infection, for example, a pesticide fumigant or a compound that stimulates synthesis of cyclic nucleotides. A phytoparasitic nematode PDE inhibitor compound of the invention may act synergistically to increase the effectiveness of one or more additional agents or treatments that can be administered to treat a phytoparasitic nematode infection or contamination. In some embodiments of the invention, a phytoparasitic nematode nematicide agent may be a previously known anti-phytoparasitic nematode agent such as a pesticide fumigant or a compound that stimulates synthesis of cyclic nucleotides. Phytoparasitic nematode PDE inhibitor compounds of the invention may be applied or administered to a plant or substrate in combination with other anti-phytoparasitic nematode agents such as other PDE inhibitor compounds of the invention, pesticide fumigants, a compound that stimulates synthesis of cyclic nucleotides, etc.

Phytoparasitic nematode PDE inhibitor compounds of the invention can be used alone or in conjugates or compositions with other molecules such as targeting agents and/or labeling agents in treatment methods of the invention. Targeting agents useful according to the methods of the invention are those that direct a compound of the invention to a specific cell type or tissue type for treatment. A targeting compound of choice will depend upon the nature of the stage of the phytoparasitic nematode infection or contamination. In some instances it may be desirable to target the PDE inhibitor compound to a plant surface, a root, a leaf, etc.; to aid a compound of the invention in accessing a plant, sticking to a plant, crossing into the plant, etc. Those of ordinary skill in the art will be aware of and able to select and use suitable targeting agents for use in methods of the invention.

In some aspects of the invention, a targeting agent is an agent that increases retention of a PDE inhibitor compound of the invention in or on a substrate, thus increasing the likelihood that the PDE inhibitor will contact a phytoparasitic nematode in or on the substrate. In some aspects of the invention, a targeting agent may be an agent that permits conversion of a PDE inhibitor compound by linkage of the compound to a peptide to alter solubility of the compound, for example to help retain the PDE inhibitor compound in or on the plant or substrate, which may increase the likelihood that the PDE inhibitor will contact a phytoparasitic nematode in or on the plant and/or substrate.

Labeling agents may be used in methods of the invention for in vitro and in vivo assays, to determine the location of phytoparasitic nematode PDE inhibitor compounds of the invention after administration or application, and may be used to assess the location of the PDE inhibitor compounds that have been administered to a plant, cell, tissue, or substrate. Procedures for attaching labels to compounds of the invention, and for and utilizing labeling agents such as enzymatic labels, dyes, radiolabels, fluorescent labels, etc. are well known in the art.

Treatment methods of the invention that include application or administration of a compound of the invention to a plant or substrate and contact of the PDE inhibitor compound with a phytoparasitic nematode can be used at any stages of a phytoparasitic nematode infection in a plant or substrate including, early-stage, mid-stage, and late-stage of the phytoparasitic nematode infection including all times before and after any of these stages. Methods of the invention may also be used for plants or substrates that have previously been treated with one or more other nematicide agents that were not successful, were minimally successful, and/or are no longer successful at slowing or stopping progression of the phytoparasitic nematode infection or contamination in or on the plant or substrate.

Treatment methods of the invention that include administration of a compound of the invention to a substrate can be used at any stage of a phytoparasitic nematode infection and can also be used in advance of potential contact with a phytoparasitic nematode, for example, as a preventive treatment. Methods of the invention may also be used for substrates that have been previously treated with one or more other compounds to treat a phytoparasitic nematode contamination that were not successful, were minimally successful, and/or are no longer successful at removing, reducing viability of, reducing infectivity of, the phytoparasitic nematodes, and/or slowing or stopping progression of the phytoparasitic nematode contamination in or on the substrate.

Effective Amounts for Treatments

Compounds of the invention are administered or applied into or onto a plant or a substrate, in an effective amount for treating the phytoparasitic nematode infection or contamination. An "effective amount for treating a phytoparasitic nematode infection" is an amount necessary or sufficient to realize a desired biologic effect. For example, an effective amount of a PDE inhibitor compound of the invention could be that amount necessary to (i) slow or halt progression of the phytoparasitic nematode infection; or (ii) reverse one or more results or effects of the phytoparasitic nematode infection. According to some aspects of the invention, an effective amount is that amount of a PDE inhibitor compound of the invention alone or in combination with another nematicide agent or treatment, which when combined or co-administered or administered alone, results in a reduction in the phytoparasitic nematode infection, either in the prevention or the treatment of the phytoparasitic nematode infection. The biological effect may be the amelioration and or absolute elimination of effects resulting from the phytoparasitic nematode infection. In another embodiment, the biological effect is the complete abrogation of the phytoparasitic nematode infection or the phytoparasitic nematodes, as evidenced for example, by an assay or test that indicates the plant and/or substrate is essentially or substantially free of the phytoparasitic nematodes and/or infection.

Assays and tests to determine the presence of phytoparasitic nematode infections are well known in the art and may include analysis of plant samples, root observation, visual assessment, etc. A non-limiting example of an assay to determine the presence of a phytoparasitic nematode infection in a plant may include observation of root nodules, plant health, etc. and/or may include microscopy, staining, detection phytoparasitic nematodes, etc. The analysis may in some embodiments include assessment of one or more samples obtained from a plant or plurality of plants, for example in a field, for the presence, absence, level, or changes of a level of one or more species of phytoparasitic nematodes. A sample from a plant or plurality of plants for diagnostic assay may be a leaf sample, root sample, etc. In some diagnostic assays or tests a sample from a plant may be cultured and then tested for the presence, absence, and/or level of a phytoparasitic nematode, or changes in the level over time, e.g., by comparison of subsequent samples with an initial sample.

Typically an effective amount of a compound of the invention to treat a phytoparasitic nematode infection will be determined in agricultural trials (for treating plants/crops), trials (for treating substrates), establishing an effective dose for a test population versus a control population in a blind study, etc. In some embodiments, an effective amount will be that which results in a desired response, e.g., an amount that diminishes a phytoparasitic nematode infection or likelihood of a phytoparasitic nematode infection in a plant or plurality of plants. An effective amount of a compound of the invention to treat a substrate may be the amount that when contacted with the substrate reduces the amount of a phytoparasitic nematode on or in the substrate. In some embodiments of the invention, an effective amount of a PDE inhibitor compound of the invention may be the amount that when contacted with the substrate reduces the likelihood that a plant contacting the treated substrate will result in the phytoparasitic nematode infection in the plant, as compared to the likelihood of an infection if the plant contacted the substrate that was not treated with the PDE inhibitor compound of the invention. Similarly, an effective amount to treat a phytoparasitic nematode infection in a plant may be the amount that when administered to the plant decreases the level of one or more phytoparasitic nematode activities in the plant to an amount that that is below the amount that would occur in the plant without the administration of the PDE inhibitor compound of the invention. In the case of treating a phytoparasitic nematode infection the desired response may be reducing or eliminating one or more effects or symptoms of the infection in a plant. The reduction or elimination may be temporary or may be permanent. The status of the phytoparasitic nematode infection can be monitored using methods of determining the amount of phytoparasitic nematode, viability of the phytoparasitic nematode, infectivity of the phytoparasitic nematode, etc. In some aspects of the invention, a desired response to treatment of the phytoparasitic nematode infection can be delaying the onset or even preventing the onset of the phytoparasitic nematode infection.

An effective amount of a phytoparasitic nematode PDE inhibiting compound of the invention to treat a phytoparasitic nematode infection (which may also be also referred to herein as a nematicide agent) may also be determined by assessing physiological effects of administration on a plant, such as a decrease of a phytoparasitic nematode infection in a subject or in or on a substrate following administration. Assays suitable to determine efficacy of a compound of the invention will be known to those skilled in the art and can be employed for measuring the level of the response to a treatment and an amount of a phytoparasitic nematode PDE inhibitor compound administered to or contacted with a plant, or an amount of a phytoparasitic nematode PDE inhibitor compound contacted with a substrate, can be modified based, at least in part, on such measurements. Assays useful to assess the effects of application or administration of a phytoparasitic nematode PDE inhibitor compound of the invention on a phytoparasitic nematode infection in a plant or crop are known in the art.

The amount of a treatment may be varied for example in a treatment of a plant or plurality of plants, by increasing or decreasing the amount of a nematicide composition, by changing the nematicide composition administered, by changing the method of application or administration, by changing the amounts applied or administered, timing of application or administration, and so on. The effective amount will vary with the particular phytoparasitic nematode infection being treated, the stage and condition of the plant being treated; the severity of the phytoparasitic nematode infection, the duration of the treatment, the specific method of application or administration, and additional factors within the knowledge and expertise of the agricultural professional or home gardener.

The effective amount of a compound of the invention in the treatment of a phytoparasitic nematode infection, treatment of a phytoparasitic nematode contamination, or in the reduction of the risk of developing a phytoparasitic nematode infection may vary depending upon the specific compound used, the mode of delivery of the phytoparasitic nematode PDE inhibiting compound, and whether it is used alone or in combination with one or more additional nematicides. The effective amount for any particular application can also vary depending on such factors as the specific phytoparasitic nematode infection or contamination being treated, the particular phytoparasitic nematode PDE inhibitor compound being applied or administered, the size of the plant, crop, or substrate, or the severity of the phytoparasitic nematode infection. A skilled artisan can empirically determine the effective amount of a particular phytoparasitic nematode PDE inhibitor compound of the invention without necessitating undue experimentation. Combined with the teachings provided herein, by choosing among various active compounds and weighing factors such as potency, relative bioavailability, substrate size and make up, plant size, crop size, severity of adverse side-effects and preferred mode of application or administration, an effective prophylactic or treatment regimen can be planned that does not cause substantial toxicity and yet is effective to treat the particular plant or substrate.

When treating a plant, a nematicide compound dosage per plant may be adjusted by an individual agricultural practitioner, particularly in the event of any complication. An effective amount typically varies from 0.01 mg/kg to about 1000 mg/kg, from about 0.1 mg/kg to about 200 mg/kg, or from about 0.2 mg/kg to about 20 mg/kg, in one or more dose applications daily, for one or more days. The absolute amount will depend upon a variety of factors including a concurrent treatment, the number of doses and the individual plant parameters including size, weather, and growing conditions. These are factors well known to those of ordinary skill in the art and can be addressed with no more than routine experimentation. In some embodiments, a maximum dose can be used, that is, the highest safe dose according to sound agricultural judgment.

When treating a substrate, the concentration of a phytoparasitic nematode PDE inhibiting compound of the invention may be applied to the substrate as a component in a composition. The concentration of a compound of the invention in a composition that is contact to the substrate and/or the final concentration of the compound of the invention in or on the substrate can be readily determined. In some embodiments of the invention, a compound of the invention may be at a concentration of at least 0.2%, 0.5%, 1%, 2%, 3%, 4%, 5%, 6%, 7%, 8%, 9%, 10%, 20%, 30%, 40%, 50%, 60%, 70%, 80%, or more weight per volume in a composition that may be applied to a substrate. In certain embodiments, it may be desirable to have a final concentration in or on a substrate in a range of from 0.1% to 33% weight to volume of a compound of the invention, including all amounts within the range.

Multiple doses of compounds of the invention are also contemplated. In some instances, a compound of the invention can be administered or applied at least daily, every other day, weekly, every other week, monthly, etc. to a plant or substrate. Doses may be administered once per day, once per week, every other week, etc.

Nematicide compounds of the invention to treat plants and/or substrates may be administered alone, in combination with other nematicide compounds of the invention, and/or in combination with other nematicide treatments that are applied to or administered to plants or substrates. Nematicide compositions for use in or on plants and/or for use on or in substrates in the foregoing methods may be, but need not be, sterile and contain an effective amount of a phytoparasitic nematode PDE inhibitor compound of the invention to produce the desired response in a unit of weight or volume suitable for application or administration to a plant and/or substrate.

The doses of a phytoparasitic nematode PDE inhibitor composition of the invention to treat a phytoparasitic nematode infection can be chosen in accordance with different parameters, in particular in accordance with the mode of application or administration used and the state of the plant or substrate. Other factors include the desired period of treatment. In the event that a response in a plant or substrate is insufficient at the initial doses applied, higher doses (or effectively higher doses by a different, more localized delivery method or route) may be employed to the extent that plant and substrate tolerance permits.

Synergistic Combinations and Treatment Methods

In some embodiments of methods of the invention, a treatment of a phytoparasitic nematode infection or contamination may include contacting a phytoparasitic nematode with a first PDE inhibitor compound and also contacting the phytoparasitic nematode with one or more additional PDE inhibitor compounds and/or one or more additional anti-phytoparasitic nematode agents. A first PDE inhibitor and an additional PDE inhibitor and/or anti-phytoparasitic nematode agent may act synergistically and thus may result in a higher level of PDE inhibition, and a greater reduction in one or more phytoparasitic nematode activities, when contacted with the phytoparasitic nematode in combination than when contacted separately. In certain embodiments of the invention, an additional anti-phytoparasitic agent is a pesticide fumigant or a compound that stimulates synthesis of cyclic nucleotides.

In some aspects of the invention, compositions are provided that comprise a phytoparasitic nematode phosphodiesterase (PDE) inhibitor compound and an additional anti-phytoparasitic-nematode agent. In such compositions the PDE inhibitor compound may be a PDE inhibitor compound that when contacted with a vertebrate control does not result in a significant negative effect on a biological function of the vertebrate control. In some compositions of the invention an anti-phytoparasitic-nematode agent is a pesticide fumigant or a compound that stimulates synthesis of cyclic nucleotides.

Formulations/Administration

Methods of this invention, generally speaking, may be practiced using any mode of administration that is agriculturally acceptable. Methods of applying pesticides are well known in the art, and may include determining dosing parameters, determining non-phototoxic dosing parameters (see for example U.S. Pat. No. 8,347,551), application modes, delivery modes, etc. An application means useful in methods of the invention may include any mode that produces effective levels of protection without causing phytotoxicity or other unacceptable adverse effects.

Phytoparasitic nematode PDE inhibitor compounds of the invention may be administered in formulations, which may be administered in phyto-acceptable solutions, which may routinely contain phyto-acceptable concentrations of salt, buffering agents, preservatives, compatible carriers, adjuvants, and optionally other nematicide or pesticide ingredients. According to methods of the invention, a phytoparasitic nematode PDE inhibitor compound may be administered in a nematicide composition. In general, a nematicide composition comprises the PDE inhibitor compound of the invention and a phyto-acceptable carrier. Phyto-acceptable carriers are well known to the skilled artisan. As used herein, a phyto-acceptable carrier means a non-phytotoxic material that does not interfere with the effectiveness of the biological activity of the active ingredients, e.g., the ability of the compound of the invention to treat the phytoparasitic nematode infection.

Phyto-acceptable carriers may include diluents, fillers, salts, buffers, stabilizers, solubilizers and other materials that are well-known in the art. Such preparations may routinely contain salt, buffering agents, preservatives, compatible carriers, and optionally other nematicide and/or pesticide agents. In certain embodiments of the invention, a nematicide composition may also include one or more agents that reduce solubility of the PDE inhibitor compound in the plant's environment or in a substrate, thereby reducing or preventing the PDE inhibitor compound from being washed away, diluted, etc. and increasing availability and of the PDE inhibitor compound in and/or on the plant or substrate and thereby increasing likelihood and/or amount of contact with the phytoparasitic nematode PDE.

Nematicide compounds of the invention may be administered directly to a plant. In some embodiments, the tissue to which the compound is administered is a plant in which the phytoparasitic nematode infection is likely to arise. Compounds may be administered once, or alternatively they may be administered in a plurality of administrations. If administered multiple times, the compounds may be administered via different routes. For example, the first (or the first few) administrations may be made directly to a plant via dusting of the plant with a material that includes the phytoparasitic nematode PDE inhibitor, while later administrations may be via an aqueous application to the plant.

Kits

Also within the scope of the invention are kits that comprise one or more compositions of the invention and instructions for use. A kit of the invention may be referred to herein as an "article of manufacture" and the terms may be used interchangeably herein. Kits of the invention may include one or more of a compound of the invention that may be used to treat a phytoparasitic nematodes infection or treat a phytoparasitic nematodes contamination. Kits containing compounds of the invention can be prepared for use in treatment methods for plants and kits containing compounds of the invention can be prepared for use in treatment methods for substrates. Components of kits of the invention may be packaged either in aqueous medium, in lyophilized form, or dry form. A kit of the invention may comprise a carrier being compartmentalized to receive in close confinement therein one or more container means or series of container means such as tubes, vials, flasks, bottles, syringes, or the like. A first container means or series of container means may contain one or more PDE inhibitor compounds of the invention. A second container means or series of container means may contain a targeting label or linker-label intermediate capable delivering a compound to a plant or substrate, etc.

A kit of the invention may also include instructions. Instructions typically will be in written form and will provide guidance for carrying-out the assay or treatment embodied by the kit and for making a determination based upon that treatment.

In some embodiments, a kit of the invention may include two or more anti-phytoparasitic nematode agents, one or more of which may be a PDE inhibitor compound of the invention. In certain embodiments, a kit of the invention may include a nematicide agent such as a pesticide fumigant and/or a compound that stimulates synthesis of cyclic nucleotides and also one or more PDE inhibitor compounds of the invention.

The following examples are provided to illustrate specific instances of the practice of the present invention and are not intended to limit the scope of the invention. As will be apparent to one of ordinary skill in the art, the present invention will find application in a variety of compositions and methods.

EXAMPLES

Example 1

Basic Local Alignment Search Tool (BLAST) searches were performed to determine whether putative Class I, II, and III PDEs were present in plants. Use of query sequences from vertebrate and invertebrate Class I PDEs, as well as a Class II (*Vibrio cholera*) and a Class III (*Dictyostelum discoidem*) PDE catalytic domain sequences, did not identify any PDE sequences in the completed genomes of *Arabidopsis thaliana* and *Oryza sativa*. This finding supports a conclusion that introduction of PDE inhibitor compounds as nematicides would likely have minimal or no adverse effects on agricultural crops that are hosts for phytoparasitic nematodes.

Phylogenetic Tree for Vertebrate and Nematode PDEs.

Figure 2:
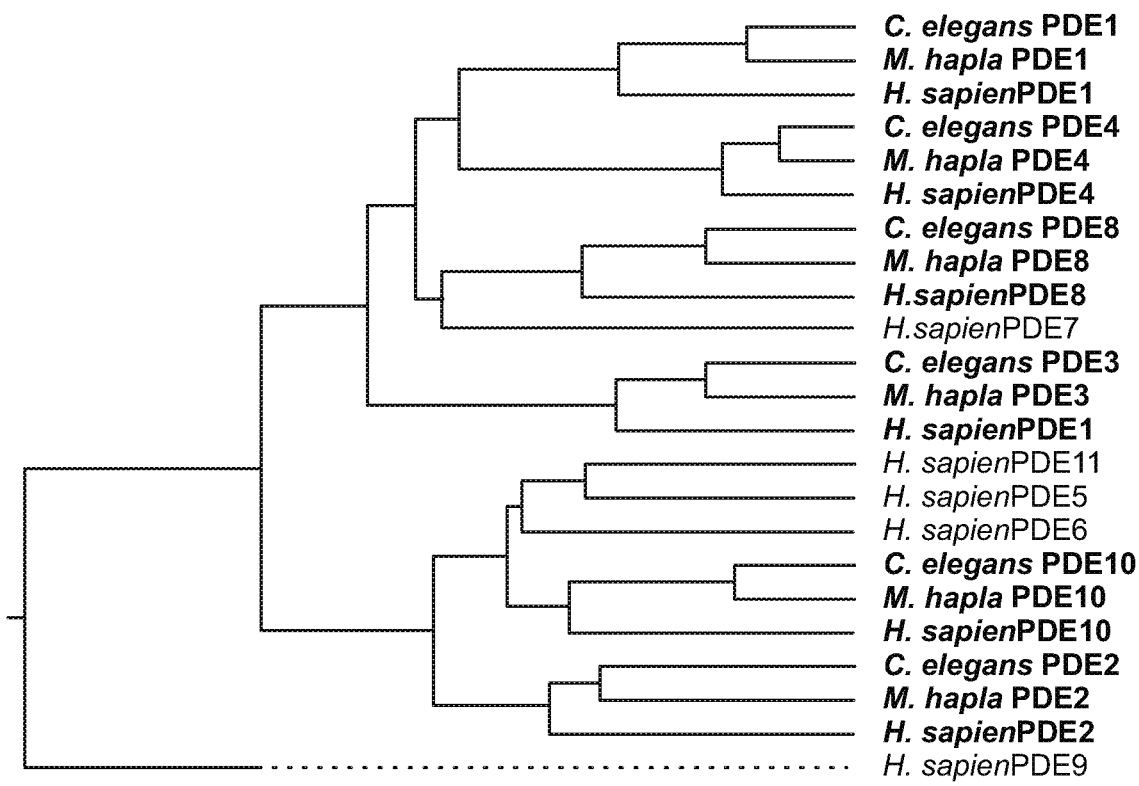
FIG. 2 provides a diagram showing a phylogenetic tree for vertebrate and nematode PDEs. Nine to 14 sequences from each vertebrate PDE family along with nematode PDE sequences from 4 *Caenorhabditis* species and from *M. hapla* were aligned and a tree generated. For simplicity only the human, *C. elegans*, and *M. hapla* sequences are represented.

Sequences from each vertebrate PDE family along with nematode PDE sequences from 4 *Caenorhabditis* species and from *M. hapla* were aligned and a tree generated (see FIG. 2). For simplicity, only human sequences, *M. hapla* sequences, and *C. elegans* sequences are represented in the figure. A listing of accession numbers for proteins used to generate the phylogenetic tree for PDE families for PDE1, PDE2, PDE3, PDE4, PDE10 (nematode PDE-5) and PDE8 (nematode PDE-6) is provided in FIG. 3. Multiple sequence alignments were done on the sets of sequences. Vertebrate species included humans, dogs, cow, rat, mouse, platypus, opossum, chicken, various fishes, and frog. Invertebrate sequences included the nematodes as well as fruit fly, sea urchin, and honeybee. If a there was not sufficient confidence in the quality of the sequence data, certain species were not included for some of the PDE families. *M. hapla* contigs for families 1-6 were 334, 111, 894, 1768, 934, and 2771 respectively. The data was downloaded through Nematode.net (see: nematode.net/NN3_frontpage.cgi?navbar_selection_home&subnav_selection=data_ftp).

Results

Identification and Classification of PDE Orthologs in Nematodes

Vertebrate genomes contain eleven PDE families (named PDE1 through PDE11). To identify and classify invertebrate PDEs, a multiple sequence alignment (CLUSTALW) was generated. The alignment included the 11 PDE genes from a phylogenetically diverse set of vertebrate species (fish, birds, amphibians, and mammals) available at NCBI. A vertebrate PDE phylogenetic tree was then generated by parsimony and neighbor joining methods.

The PDEs present in the *Caenorhaditis* spp. genomes were categorized with reference to the vertebrate PDE phylogeny, and it was confirmed that *C. elegans* (and other species in this genus) contains six PDEs orthologous to the following vertebrate families: PDE1, PDE2, PDE3, PDE4, PDE10 [referred to as PDE-5 in Wormbase; (2013) and PDE8 [referred to as PDE-6 in Wormbase (2013). Because sequence information for *Meloidogyne* spp. was not available in curated databases, full-length open reading frames were assembled for six PDE genes from the *M. hapla* genome (accessed through nematode.net) through BLAST searches with human and *C. elegans* sequences as queries. It was found that *M. hapla* contains the same six PDE families as the *Caenorhabditis* spp. (FIG. 2).

In addition to the complete gene sequences for the nematodes described above, BLAST searches identified partial sequence information for PDEs in many other phytoparasitic nematodes, including *M. incognita* (PDE1, PDE3, PDE4, PDE8, and PDE10), *M. chitwoodi* (PDE8), *Heterodera glycines* (PDE1, PDE3, PDE4), and *H. schactii* (PDE3).

Saturated Evolutionary Trace Analysis Reveals Functionally Important PDE Inhibitor Binding Sites in Nematode PDEs After all of the PDEs were classified, each of the six nematode PDE families was analyzed by saturated evolutionary trace (SET) analysis [see Lichtarge and Sowa (2002); Carleton et al. (2005); Cahill et al. (2012)]. SET analysis was used to identify unanimous sites (identical amino acid in every vertebrate and invertebrate sequence analyzed) and class-specific sites (an invariant amino acid in every vertebrate sequence within a PDE family and a different, invariant amino acid present in every nematode sequence of the same PDE family). As shown in Table 2, 22-38% of the amino acids in the catalytic domain are identical (unanimous) in all species examined for each of the six PDE families. The high degree of sequence conservation suggested that the catalytic and pharmacological properties of nematode PDEs are likely to be similar to the vertebrate orthologs.

A significant number of residues (class-specific sites) were identified as evolutionarily conserved within a vertebrate PDE family or within a nematode PDE family, but which had a different amino acid at this position when comparing vertebrates and nematode sequences. These class-specific sites are particularly important for identifying differences in inhibitor binding between vertebrate and nematode PDEs.

TABLE 2

Saturated Evolutionary Trace (SET) analysis of nematode PDE catalytic domains.

| Vertebrate PDE Family | % Unanimous (V = N) | % class-specific (V ≠ N) |
| --- | --- | --- |
| PDE1 | 25% | 4% |
| PDE2 | 25% | 9% |
| PDE3 | 30% | 6% |
| PDE4 | 38% | 8% |
| PDE10 | 22% | 15% |
| PDE8 | 25% | 12% |

Note:
In this SET analysis of nematode PDE catalytic domains, unanimous sites are sites where the same amino acid was found in every sequence in the multiple sequence alignment. Class-specific sites are sites where all vertebrate (V) sequences had an invariant amino acid at that position, and nematode (N) sequences had a different (but invariant) amino acid at the same position.

Figures 5, 6:
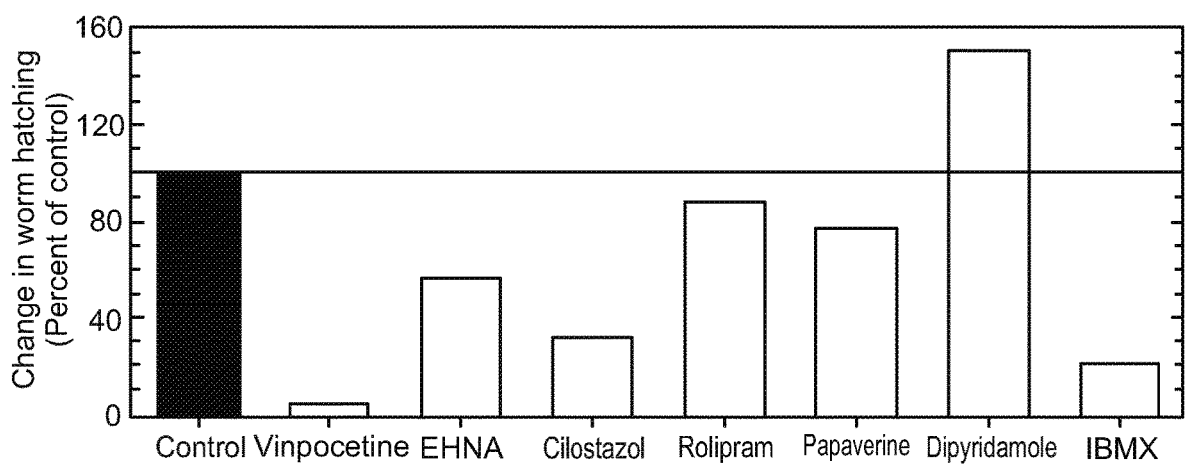
FIG. 5 provides a data key that can be used to identify the position of each of the listed residues, relative to the human sequences whose accession numbers are in the second to bottom box of each column. Protein Data Bank (PDB; www.rcsb.org) structure file identification numbers are provided in the bottom box of each column of FIG. 5.
FIG. 6 provides a graph showing changes in worm egg hatching after exposure to various PDE inhibitors or control (i.e., worms that did not contact a PDE inhibitor). Nematodes were allowed to progress to adulthood (~4 days) and produce eggs at room temperature while exposed to PDE inhibitors at concentrations maximally reducing motility. The number of newly hatched juveniles on Day 5 was counted and normalized to the reproductive success of the control condition (no inhibitor). This experiment was performed once.

FIG. 4 shows results of SET analysis that identified unanimous sites (identical amino acid in every vertebrate and invertebrate sequence analyzed) and class-specific sites (an invariant amino acid in every vertebrate sequence within a PDE family and a different, invariant amino acid present in every nematode sequence of the same PDE family) for amino acid residues believed to be involved in binding of the indicated PDE inhibitor compound. The groups of identifiers (e.g. for PDE2 the nematode, vertebrate, and IBMX interaction sites are listed on the left, residues are shown and specific differences between residues at these locations are shown. For example, for PDE3 it can be seen that *Meliodogyne hapla* and *Caenorhabditis* spp. both have the amino acid "S" position highlighted and under and to the left of the number "421". In contrast, vertebrate PDE3 has amino acid "G" in that corresponding position. In another example, it can be seen that *Meliodogyne hapla* PDE4 has amino acid "L" in the position shown to the left and below the number "437" but *Caenorhabditis* spp. PDE4 has amino acid "M" in that corresponding position. In FIG. 4, two boxes are shown that indicate residues that are only in *Meliodogyne hapla* at that position and are not found in the corresponding position in *Caenorhabditis* spp. or the drug interaction site between PDE4-roflumilast or PDE4-rolipram. These boxes are shown FIG. 4 in the *Meliodogyne hapla* PDE3 row, beneath AA residue number 176 and in the *Meliodogyne hapla* PDE4 row beneath AA residue number 437. A data key was prepared and shown as FIG. 5. FIG. 5 can be used to identify the position of each of the listed residues, relative to the human sequences whose accession numbers in the second to bottom box of each column of FIG. 5. PDB structure file identification is provided in the bottom box of each column of FIG. 5.

Each residue position set forth in FIG. 4 can be identified using the information provided in FIG. 5. For example, the first box under PDE2 IBMX column in FIG. 5, lists L809 and the end of the column indicates that the number is in reference to the *Homo sapiens* sequence having Accession number NP_000408. L809 is the location of the first amino acid "L" listed for PDE2 IBMX interactions in FIG. 4, thus, the "L" listed for nematode PDE 2 and vertebrate PDE2 in FIG. 4, are in each of their respective sequences at positions that correspond to the position of residue 809 in accession number NP_000408. The position of each amino acid listed in FIG. 4 can be identified using the key provided in FIG. 5. Thus, using alignments of sequences having accession numbers in FIG. 3, and the key provided in FIG. 5, the position of each amino acid listed in FIG. 4 can be determined. FIG. 4 provides examples of locations at which binding differences may be exploited to select compounds that will selectively and/or specifically bind to a PDE.

Structural Analysis of Inhibitor Binding to PDE Catalytic Sites

To evaluate whether PDE inhibitors designed to bind to human PDEs are likely to bind to nematode PDEs, available crystal structures of PDEs complexed with inhibitors were examined. The existing structures reveal which amino acid residues in the enzyme active site stabilize inhibitor binding. As a representative example, human PDE4 binding to a PDE4-selective inhibitor, rolipram, can be visualized [Burgin et al., (2010)]. Of the nine human PDE4 residues directly interacting with rolipram, 7 are identical to the residues present in nematode PDE4. For PDE3 and PDE10, 3 out of 18 and 1 out of 5 drug interaction sites, respectively, have been identified where class-specific differences occur between vertebrate and nematode PDEs.

Example 2

Preliminary results suggest that observed differences between nematode and vertebrate PDE catalytic domain amino acid sequences may result in altered sensitivity of nematode PDEs toward selective PDE inhibitors. The pharmacological properties of *C. elegans* and *M. hapla* PDE catalytic domains are characterized with a set of family-selective PDE inhibitor compounds. These experiments may identify family-specific PDE inhibitor compounds useful for evaluating the physiological consequences of disrupting cyclic nucleotide metabolism in the free-living nematode *C. elegans* and the phytoparasitic nematode *M. hapla*.

Methods to Sub-Clone and Express the Catalytic Domains of Selected PDEs from *C. elegans* and *M. hapla*.

It is known that catalytic domains from most vertebrate PDE families can be expressed as recombinant proteins. Experiments are performed to express nematode PDE catalytic domains in a bacterial expression system in a catalytically active form. The open reading frames of nematode PDE catalytic domains are subcloned into bacterial expression vectors, and the recombinant proteins affinity purified for analysis.

The N- and C-terminal boundaries of the catalytic domain of each PDE family are determined by comparing the human PDE crystal structure with the protein sequence alignment of the orthologous nematode PDE. Synthetic catalytic domain DNA is codon-optimized for expression in *E. coli*, and cloned into bacterial expression vectors (pET and pGEX plasmids) containing N-terminal fusion protein tags. Expression conditions are optimized by varying the concentration of the inducer (IPTG), *E. coli* expression strain, temperature, and/or duration of expression. Hexahistidine-tagged proteins or glutathione-S-transferase (GST)-tagged fusion proteins are purified by affinity chromatography on Ni-NTA or glutathione-coupled beads. All constructs are sequence-verified prior to use.

Determining the Kinetic and Pharmacological Properties of Nematode PDEs.

Results of phylogenetic and structural comparisons of vertebrate and nematode PDE catalytic domains described above suggest that nematode PDEs will retain the general enzymatic properties (e.g., substrate specificity) characteristic of their vertebrate orthologs but may differ in their pharmacological sensitivity to certain inhibitor compounds. Enzymatic assays are conducted to define the substrate specificity of the nematode enzymes. Dose-response relationships for family-specific PDE inhibitor compounds are evaluated to assess the affinity of these compounds for both *C. elegans* and *M. hapla* PDE family members.

Methods

Construction and Expression of Nematode PDE Catalytic Domains Enzymatic and Pharmacological Analyses:

Purified PDE catalytic domains are assayed for the rate of cyclic nucleotide hydrolysis over a range of substrate concentrations to determine the Km (substrate preference) and kcat (turnover number) for each PDE. Radiotracer assays are used to quantify hydrolytic rates [D'Amours and Cote, (1999); Cote (2000)]. Dose-response relationships for each nematode PDE are performed using a set of commercially available, family-specific inhibitor compounds (see for example, compounds in Table 1). This provides estimates of the IC50, the inhibition constant (Ki), and the selectivity ratio (defined as the ratio of the Ki value of a drug for two different PDEs) for each inhibitor assayed for each nematode PDE family [Zhang et al., (2005)].

Example 3

Evaluation of the Ability of PDE Inhibitors to Prevent Hatching of *C. elegans* Eggs To assess disruption of activities such as developmental progression leading to egg hatching in nematodes, *C. elegans* eggs are exposed to PDE inhibitors. The nematode eggs are exposed to a range of concentrations of family-specific PDE inhibitors, and inhibitors that prevent egg hatching are identified. Results of the testing with various PDE inhibitors are shown in FIG. 6.

Assays to Determine Efficacy of PDE Inhibitor Compound in Disrupting Chemosensation Pathways in Larvae and Adult Stage Nematodes Such as *C. elegans* or a Phytoparasitic Nematode.

Experiments are performed to identify whether disrupting cyclic nucleotide signaling pathways involved in locomotion and/or chemotaxis with PDE inhibitors results in paralysis, uncoordinated movement, and/or inability to respond to chemical gradients. Using tracking assays, PDE inhibitor compounds that are effective in disrupting chemotaxis in *C. elegans* and/or phytoparasitic nematodes were identified.

Methods:

Culturing *C. elegans*:

Wild-type Bristol N2 *C. elegans* strain were used for initial experiments and all nematodes were cultured using standard methods [Brenner, (1974)]. Adult nematodes were grown on nematode growth media plates to the gravid stage where their bodies are filled with eggs and are then treated with sodium hypochlorite to isolate the eggs. Isolated eggs are used immediately in assays or cultured without a food source to obtain dauer larvae. When these dauer nematodes are given *Escherichia coli* OP50 for their food source, they progress out of the dauer state and into additional stages until reaching adulthood.

Treatment of Eggs and Dauer State Larvae with PDE Inhibitors:

Eggs and dauer state larvae were exposed to a series of concentrations of a PDE inhibitor compound in suspension, following established methods [O'Halloran et al; Lin et al., (2013)]. For the case of dauer larvae, the juveniles are suspended in solutions containing PDE inhibitor compounds, and then plated on agar containing the same inhibitor concentration. In some tests, nematodes (both eggs and larvae) were constantly exposed to a defined drug concentration throughout the course of the assays.

Quantitation of Egg Hatching:

The number of hatched larvae in the treated group was compared to a control (untreated) group and the results are evaluated as a function of time up to 3 days after exposure to the PDE inhibitor.

Chemotaxis Assays:

*C. elegans* are attracted to anions, cations, alkaline pH and odorants [Ward, (1973); Bargmann et al., (1993); L'Etoile et al., (2002)]. The ability of *C. elegans* L2 larvae to migrate toward an attractant [either salt (Kano et al., 2008 or pH (Matsuura et al., 2010)] in the presence or absence of PDE inhibitors is tested. The number of unresponsive nematodes is counted in order to measure mortality.

Salt gradient: A salt gradient is established on agar plates by initially spotting (20 h prior to testing to allow for diffusion into the agar) 50 mM NaCl; a mock control spot is also placed at the opposite pole of the plate. After exposure to inhibitor, 25 dauer state nematodes are placed on the center of the salt gradient agar plate and worm movement is assessed every 10 min for 4 hr.

pH gradient: The experimental protocol is similar to the salt gradient, this time using 1 M sodium acetate to generate the chemical gradient.

Worm motility and directionality toward an attractant point source is quantified using a Nikon AZ100 dissecting microscope equipped with a video camera. Worm movement is quantified using worm tracking software packages currently available [e.g., Ramot et al., (2008)].

Example 4

Evaluating the Ability of PDE Inhibitors to Prevent Hatching of *M. hapla* Eggs.

To assess whether inhibitor compounds specifically targeting individual PDE enzyme families will retard or prevent developmental progression from egg to infective juvenile phytoparasitic nematodes, *M. hapla* eggs are exposed to PDE inhibitors and the ability of eggs to hatch is determined and compared to the hatching ability in untreated control groups.

Determining the Effects on Chemotaxis of *M. hapla* Juveniles Exposed to PDE Inhibitors.

Studies are conducted to assess whether PDEs implicated in locomotion and chemosensation in *C. elegans* are targets for disrupting chemotaxis in the juvenile stage of *M. hapla* upon exposure to family-specific PDE inhibitors. Using time-lapse photography, the movement of J2 juveniles is tracked and the effects of PDE inhibitors on the ability of *M. hapla* juveniles to respond to chemical attractants are quantified.

Assessing the Ability of PDE Inhibitors to Prevent *M. hapla* Juveniles from Infecting Plant Roots.

Studies are conducted to assess the ability of one or more PDE inhibitors to reduce the ability of infective *M. hapla* J2 juveniles to migrate to the plant root and parasitize its host. Using *A. thaliana* seedlings as a model system, *M. hapla* juveniles are treated with PDE inhibitors and their ability to migrate to *A. thaliana* roots and to infect the host is quantified.

Methods

*M. hapla* Egg Collection:

*M. hapla* eggs are collected using standard methods [see for example, (Wang et al., 2009) (Fudali et al., 2013). Briefly, tomato cultivars are infected by *M. hapla* and allowed to produce progeny. Eggs are collected and are concentrated by sucrose flotation, surface sterilized (Nitao et al., 1999), and then added to an aqueous suspension to induce hatching.

Treatment of *M. hapla* Eggs and J2 Juveniles with PDE Inhibitors:

These methods follow a similar protocol as described for *C. elegans* in Example 3, except that J2 juveniles are added to Pluronic F-127 gel (not agar) that has been supplemented with the same concentration of inhibitor.

Quantitation of Egg Hatching:

Assays are performed to quantify the effect of treatment with PDE inhibitors on egg hatching of *M. hapla* (Nitao et al., 1999) (Talavera and Mizukubo, 2005). The number of hatched J2 nematodes in the treated group compared to the control (untreated) group is evaluated as a function of time up to 7 days.

Chemotaxis and Mortality Assay:

Infective J2 juveniles of *M. hapla* are attracted to low pH (~5). This attraction is employed in an in vitro chemotaxis assay that measures the migration of *M. hapla* in a Pluronic F-127 gel in response to a pH gradient (Wang et al., 2009). Using time-lapse photography described in Example 3, the migration of *M. hapla* juveniles treated with PDE inhibitor compounds in a pH gradient is recorded over a period of 10 h, and compared to control animals not exposed to the PDE inhibitor. The number of immobile and unresponsive nematodes is also determined in order to quantitate paralysis and mortality.

Root Attraction Assay:

The ability of infective *M. hapla* J2 juveniles to migrate to a plant root is initially evaluated using root tips of *Arabidopsis thaliana* and other species (Fudali et al., 2013).

Root Infectivity Assay:

After completion of the root attraction assay, infected roots are stained with acid fuchsin to visualize *M. hapla* juveniles inside the seedling root (Wang et al., 2009). The fraction of nematodes that successfully infect plant roots once in the vicinity of the root is quantified.

Example 5

The following experiments tested whether compounds that specifically inhibit different phosphodiesterase (PDE) enzyme families in vertebrate will perturb in vivo cyclic nucleotide metabolism in *C. elegans* and result in an observable behavior/physiological response.

Experiments were performed to examine the time course of exposure of worms to seven different PDE inhibitors at their highest soluble concentration to evaluate the extent to which the inhibitor compound was effective in reducing worm motility.

Methods

The ability of these various PDE inhibitors to reduce the fecundity of *C. elegans* was also examined. To do this, the number of newly hatched juveniles under control conditions was compared to the number of newly hatched juveniles that had been continuously exposed to PDE inhibitors for the duration of the experiment. As shown in FIG. 6, vinpocetine, IBMX, and cilostazol were the most effective in preventing egg hatching, whereas dipyridamole actually enhanced egg hatching under the experimental conditions.

Summary

These preliminary data support a conclusion that exposing nematodes to selective phosphodiesterase (PDE) inhibitors will alter intracellular signaling pathways responsible for nematode motility and reproduction. More specifically, these results demonstrated the feasibility of studies to evaluate the efficacy of PDE inhibitors to disrupt the lifecycle of nematodes in vivo and to determine the physiological consequences of exposure of *M. hapla* to selective PDE inhibitors in vivo. The results of these studies support the idea that phosphodiesterase (PDE) inhibitors may serve as "next-generation" nematicides for the purposes of managing plant parasitic nematodes.

Example 6

Physiological Effects

Several PDE inhibitors specific towards each enzyme family were tested to determine which compounds are most effective in reducing nematode motility. It was found that cilostazol and milrinone (PDE3 inhibitor), rolipram (PDE4 inhibitor), and papaverine and MP10 [PDE10 inhibitor, also referred to as PF-2545920, (Selleck Chemicals, Houston, Tex.)] were most effective in reducing motility in the dauer state of *C. elegans*. All these drugs were able to reduce normal nematode motility by about 70-80%. The nematodes became uncoordinated or immotile when exposed to these drugs. Reversibility studies showed that drug effects were reversed after 24 hours (all nematodes recovered). The dauer state is morphologically similar to the infective states in juvenile phytoparasitic nematodes.

Asynchronous Vs. Dauer Inhibition

Figure 7:
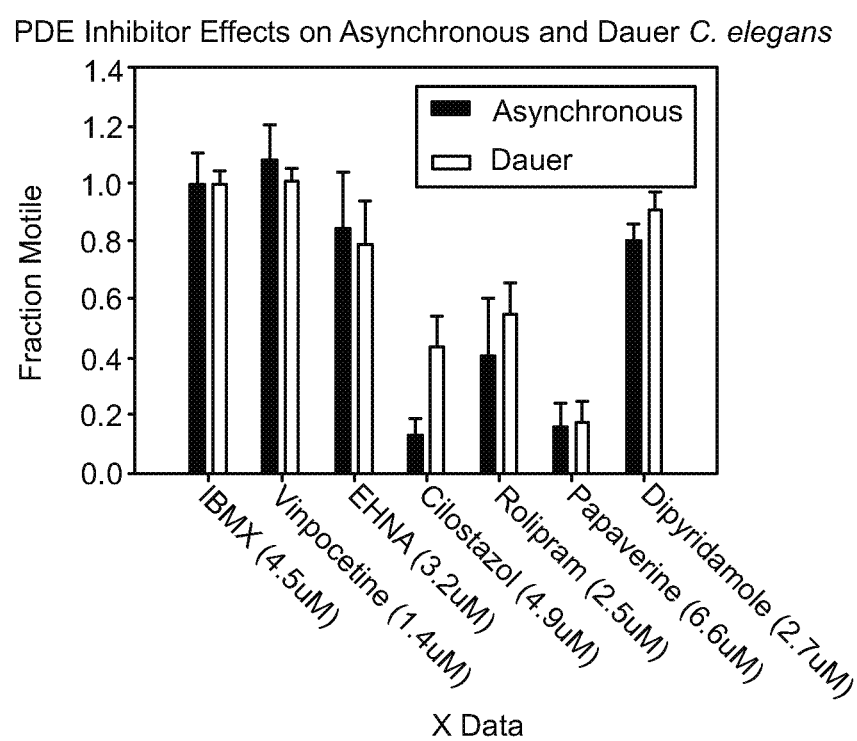
FIG. 7 shows a graph of results of the effects of various PDE inhibitors on worm motility in which an asynchronous population of nematodes or a population of dauer nematodes were compared. Testing was performed after contact with IBMX, vinpocetine, EHNA, cilostazol, rolipram, papaverine, or dipyridamole at the concentrations indicated on the figure. Solid black bars represent the asynchronous population. The grey bars represent the dauer state population. The experiment was repeated three times and the data points represent the mean plus and minus the standard deviation.

Different stages of nematodes were tested for effectiveness of PDE inhibitors at reducing motility. Results are shown in FIG. 7 from testing of the effect of various inhibitors in asynchronous and dauer state nematodes. Motility was determined after contact with the indicated concentration of IBMX, vinpocetine, EHNA, cilostazol, rolipram, papaverine, or dipyridamole. Dauer nematodes are motile non-feeding worms in an arrested state. The dauer nematodes were obtained through a bleach solution that kills the live worms but allows the eggs to remain unaffected. The eggs were then allowed to hatch in the absence of food to obtain dauer worms. Asynchronized nematode populations were obtained from plates ~5 days old with worms of different developmental states. Exposure/treatment of the dauer and asynchronized nematodes were the same. With the exception of cilostazol, asynchronized populations showed similar sensitivity to PDE inhibitor compounds as nematodes arrested in the dauer state.

Dose-Response Testing

Figure 8:
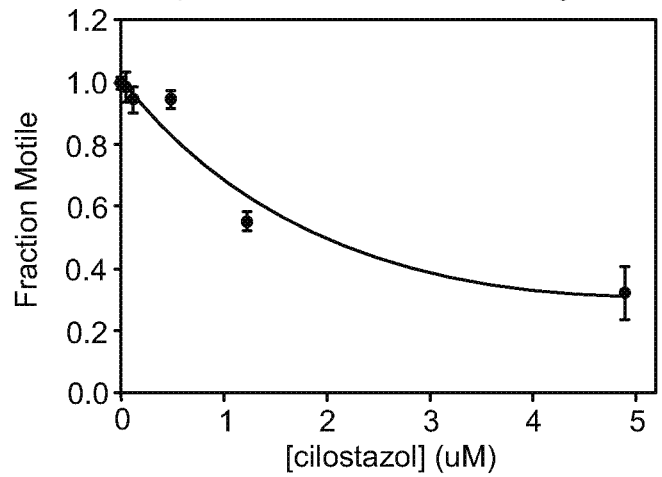
FIG. 8 shows a dose-response graph for cilostazol (a PDE3 inhibitor). The graph indicates the micromolar (μm) concentration of cilostazol and the fraction of motile worms relative to control worms not contacted with cilostazol. The experiment was repeated three times and the data points represent the mean plus and minus the standard deviation.
Figure 9:
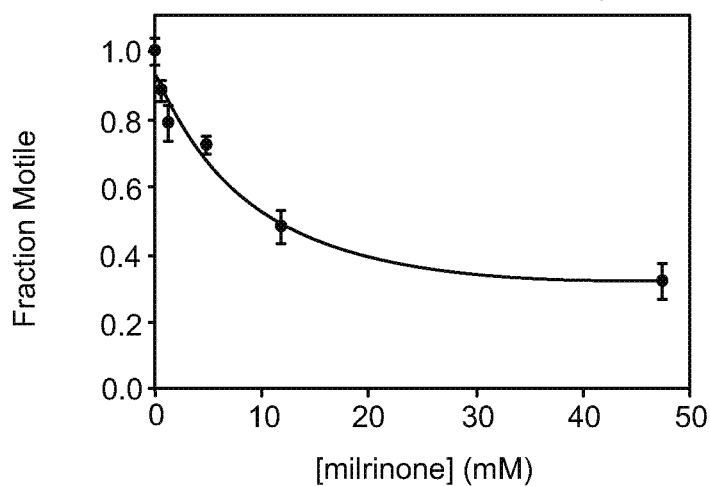
FIG. 9 shows a dose-response graph for milrinone (a PDE3 inhibitor). The graph indicates the millimolar (mM) concentration of milrinone and the fraction of motile worms relative to control worms not contacted with milrinone. The experiment was repeated three times and the data points represent the mean plus and minus the standard deviation.
Figure 10:
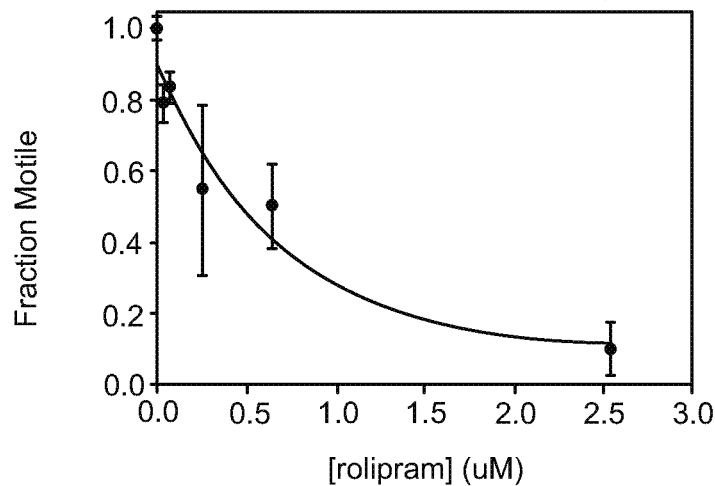
FIG. 10 shows a dose-response graph for rolipram (a PDE4 inhibitor). The graph indicates the micromolar (μM) concentration of rolipram and the fraction of motile worms relative to control worms not contacted with rolipram. The experiment was repeated three times and the data points represent the mean plus and minus the standard deviation.
Figure 11:
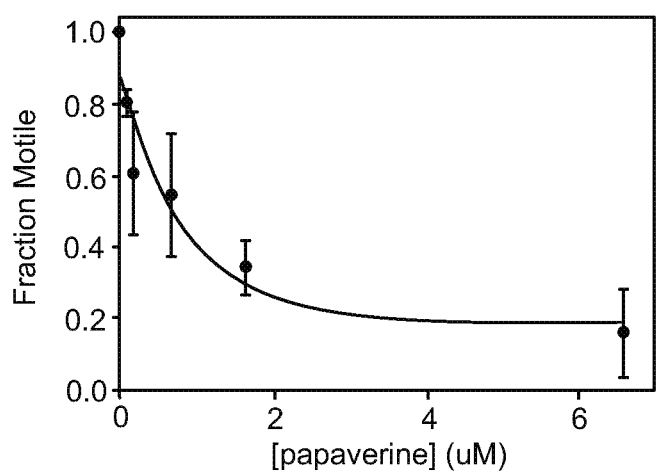
FIG. 11 shows a dose-response graph for papaverine (a vertebrate PDE10 inhibitor). The graph indicates the micromolar (μM) concentration of papaverine and the fraction of motile worms relative to control worms not contacted with papaverine. The experiment was repeated three times and the data points represent the mean plus and minus the standard deviation.
Figure 12:
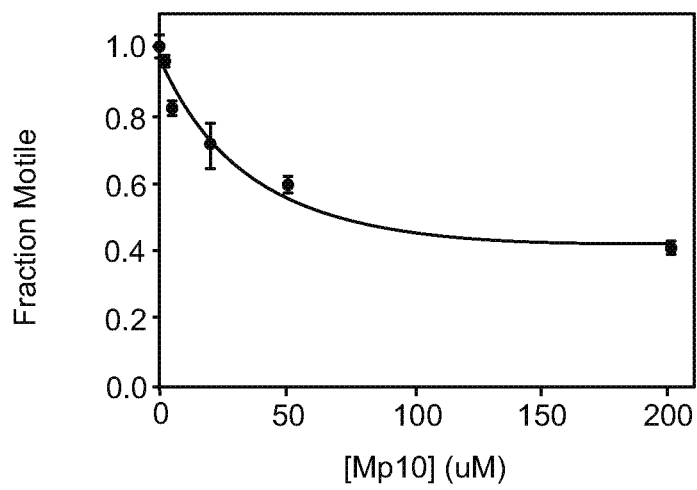
FIG. 12 shows a dose-response graph for MP10 (a vertebrate PDE10 inhibitor). The graph indicates the micromolar (μM) concentration of MP10 and the fraction of motile worms relative to control worms not contacted with MP10. The experiment was repeated three times and the data points represent the mean plus and minus the standard deviation.

Dose-response relationships were performed (with dose-response testing methods set forth in Example 5) to quantify the potency of drugs. Results from dose-response testing are shown in FIGS. 8-12, which show dose-response graphs for cilostazol (FIG. 8), milrinone (FIG. 9), rolipram (FIG. 10), papaverine (FIG. 11), and MP10 (FIG. 12). FIG. 8 shows a dose-response graph for cilostazol (a PDE3 inhibitor). The graph indicates the micromolar concentration of cilostazol and the fraction of motile worms relative to control worms not contacted with cilostazol. FIG. 9 shows a dose-response graph for milrinone (a PDE3 inhibitor). The graph indicates the millimolar concentration of milrinone and the fraction of motile worms relative to control worms not contacted with milrinone. FIG. 10 shows a dose-response graph for rolipram (a PDE4 inhibitor). The graph indicates the micromolar µM concentration of rolipram and the fraction of motile worms relative to control worms not contacted with rolipram. FIG. 11 shows a dose-response graph for papaverine (a PDE10 inhibitor). The graph indicates the micromolar µM concentration of papaverine and the fraction of motile worms relative to control worms not contacted with papaverine. FIG. 12 shows a dose-response graph for MP10 (a PDE10 inhibitor). The graph indicates the micromolar µM concentration of MP10 and the fraction of motile worms relative to control worms not contacted with MP10.

Study of the Time Course of the PDE Inhibitor Effect on Motility

Figure 13:
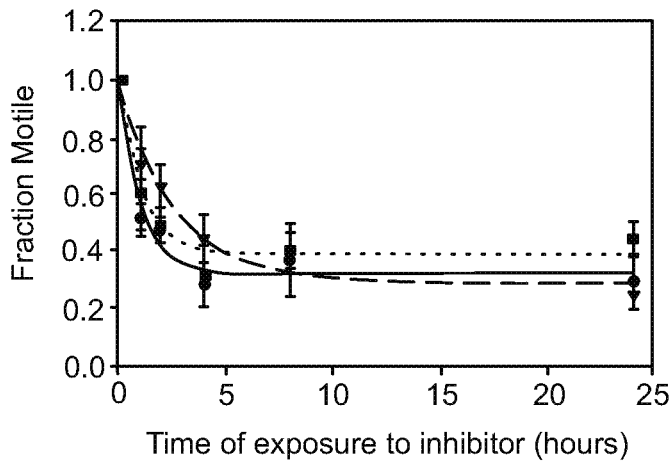
FIG. 13 provides a graph showing results of a study to determine the time course of PDE inhibitor effects on worm motility following contact with the inhibitor compound. The time is shown in hours after contact was initiated and the effect was determined by assessing the fraction of contacted worms that were motile, relative to control worm motility (i.e., motility of worms not contacted with tested drug). Cilostazol (circles and solid line), rolipram (squares and dotted line) and papaverine (triangles and dashed line) were tested. The experiment was repeated three times and the data points represent the mean plus and minus the standard deviation.
Figure 14A:
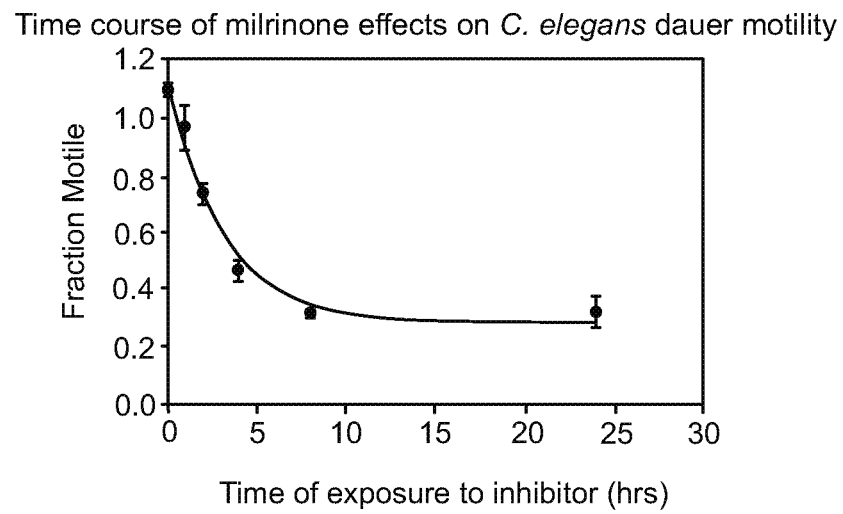
FIG. 14 shows graphs of results of a study to determine the time of drug effect on worm motility after contact with milrinone (FIG. 14A) and MP10 (FIG. 14B). The time is shown in hours after contact and the effect was determined by assessing the fraction of contacted worms that were motile, relative to control worm motility (i.e., motility of worms not contacted with the tested drug). The X-axis shows times at which motility was evaluated and the Y-axis shows the fraction of all worms that exhibited normal motility. The experiment was repeated three times and the data points represent the mean plus and minus the standard deviation.
Figure 14B:
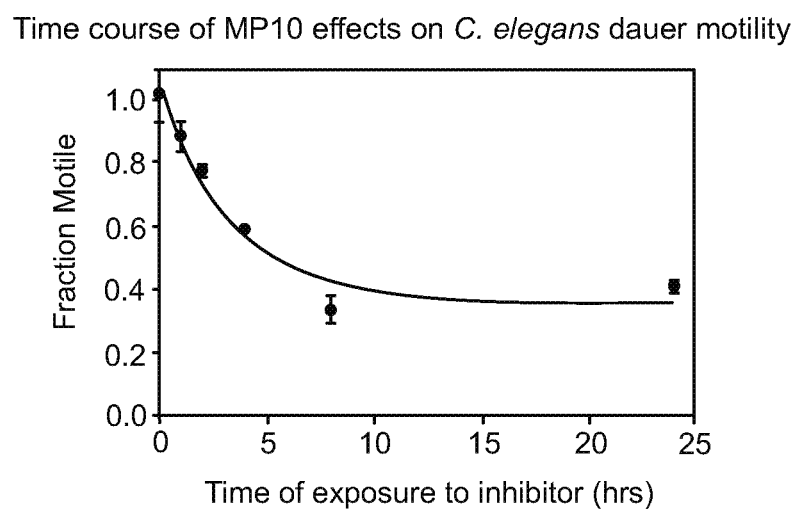

For this study, worms were contacted with drugs and scored for motility at various time points after the drug treatment to determine how quick the motility defect occurred. Nematodes were scored at 0, 1, 2, 4, 8, and 24 hours after addition of the treatment. Concentrations were 4.9 µM cilostazol, 2.5 µM Rolipram, and 6.6 µM papaverine. FIG. 13 provides a graph showing results of study to determine the time of drug effect on worm motility after contact. The time is shown in hours after contact was initiated and the effect was determined by assessing the fraction of contacted works that were motile, relative to control worm motility (i.e., worms not contacted with the tested drug). Cilostazol, rolipram and papaverine were tested. FIG. 14 shows graphs of results of study to determine the time of drug effect on worm motility after contact with milrinone (FIG. 14A) and MP10 (FIG. 14B). The time is shown in hours after contact and the effect was determined by assessing the fraction of contacted works that were motile, relative to control worm motility (controls were worms not contacted with tested drug). In the graph, the X axis shows the time after initial contact of the worms to the PDE inhibitor at which motility was evaluated and the Y axis shows the fraction of worms that exhibited normal motility in comparison to the control condition (i.e., no contact with PDE inhibitor).

Recovery after Drug Treatment

Figure 15:
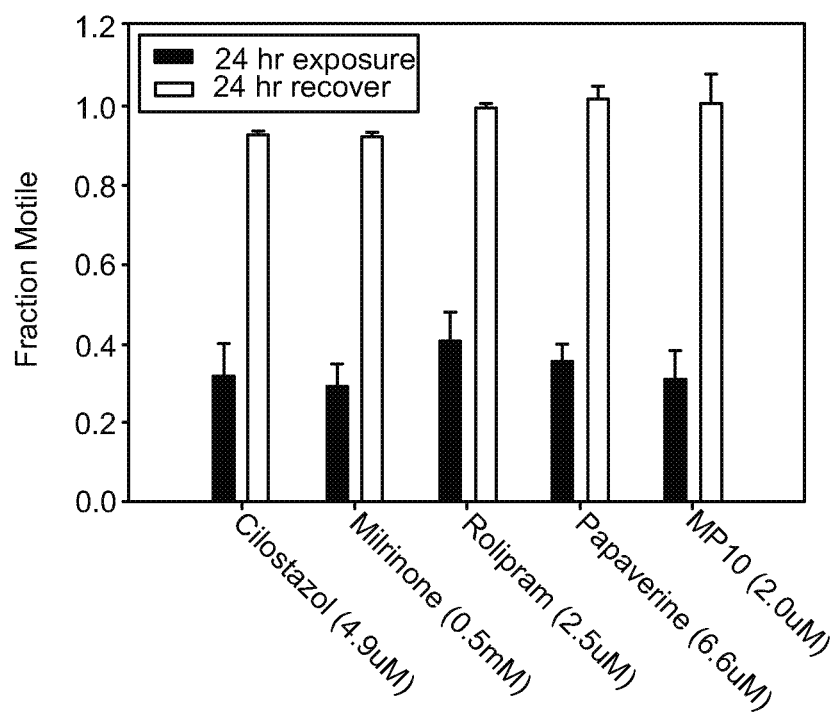
FIG. 15 shows a graph of recovery of motility after contact with a PDE inhibitor ceased. The results show the fraction of total worms with altered motility after drug contact and the fraction of worms that recovered normal motility after contact with the following inhibitors ceased: cilostazol, milrinone, rolipram, papaverine, and MP10. Motility is shown relative to the control condition (i.e., motility of worms not contacted with the test drug). The black bars represent the fraction of motile worms after 24 hours of exposure to the PDE inhibitor. The grey bars represent the fraction of motile worms 24 hours after the exposure to the inhibitor ceased. The experiment was repeated three times and the data points represent the mean plus and minus the standard deviation.

This study was performed to determine whether motility defects that resulted from contact with PDE inhibitors were permanent or temporary. For the study, nematodes were exposed for 24 hours with the PDE inhibitor (at the concentration indicated in FIG. 15) and then plated out and evaluated for normal motility as described elsewhere in the Examples. The inhibitor was then removed from the medium in which the worms were maintained, and 24 hours thereafter the fraction of worms exhibiting normal motility was evaluated. FIG. 15 shows the effects of PDE inhibitors on worm motility and the extent to which the inhibitor effect was reversible 24 hours after the inhibitor compound was removed from contact with the nematodes, using the following inhibitors: cilostazol, milrinone, rolipram, papaverine, and MP10. Motility is shown relative to control motility in worms not contacted with the test drug.

Example 7

Bioinformatic Analysis of *Heterodera glycines* PDE3 Catalytic Domain Sequence

The alignment in FIG. 16 shows that many amino acid residues are conserved between the nematode and vertebrate PDE3 family. This information shows that *Heterodera glycines* is susceptible to control by a PDE inhibitor. Additional parasitic nematode species susceptible to control by the methods herein described are identified. Genomic data from parasitic nematode species are obtained and compared against known PDE sequences. Such comparisons are done by sequence alignment tools such as BLAST, ClustalW2, FASTA, or any other sequence alignment or pairwise alignment tool, or by a motif finding tool, or any other tool or method by which sequences may be compared. Catalytic domains are identified based on sequence similarity and sequence analogy to the known catalytic domains of PDE enzymes from eukaryotic organisms. As used herein, "sequence analogy" means one or more amino acid sequences whose amino acid residues are functionally conserved within the catalytic domain of a known enzyme. The amino acid sequences need not be identical or merely similar. Rather, an amino acid sequence with sequence analogy to another sequence maintains functionally similar amino acid residues located at functional positions within the catalytic domain.

Specific PDE inhibitor compounds are designed to bind to the amino acid residues located at the functional positions of the catalytic domain of the PDE enzyme of a parasitic nematode species. The specific PDE inhibitor compounds thus designed bind with the parasitic nematode PDE, and thereby control a parasitic nematode infestation. Genomic data available for *Heterodera glycines* was examined and partial sequence information for PDEs 1, 2, 3, 4, 8, and 10 was identified in this species. In addition, a nearly full-length catalytic domain sequence for PDE3 was predicted from the genomic information. FIG. 16 shows the alignment of PDE3 amino acid sequences from *Meloidogyne* [MHA PDE3 (SEQ ID NO:1), contig 894], *Heterodera*. [HGL PDE3 (SEQ ID NO:2), U.S. Pat. No. 8,067,671 sequence 143193)], *C. elegans* [CEL PDE3 (SEQ ID NO:3), Accession number NP 001254453], and human [HSA PDE3 (SEQ ID NO:4), Accession number NP 000913]. The alignment in FIG. 16 shows that many amino acid residues are conserved between nematodes and vertebrates, including *H. glycines*. This information shows that *Heterodera glycines* may be susceptible to control by a PDE inhibitor.

Example 8

*Meliodogyne* and *Heterodera* nematodes are contacted with a PDE inhibitor. Levels of one or more activities in the contacted nematodes are determined and compared to the one or more activity levels in control *Meliodogyne* and *Heterodera* nematodes that are not contacted with the PDE inhibitor. One or more activity levels including motility (e.g., locomotion), hatching, development, chemosensation, chemotaxis, infectivity, viability, reproduction, replication, invasion of a host, or establishment of a parasitic infection in a host are determined using methods descripted in the Examples herein. In certain studies, the nematodes are contacted and assessed in vitro, for example in culture. In additional studies the nematodes are contacted in or on plants, which may be cultivated in a laboratory setting or may be crop plants, e.g., field-grown plants or crops.

In some studies, the PDE inhibitor is a PDE inhibition that does not result in a significant level of PDE inhibition in a vertebrate and/or vertebrate sample when the inhibitor is contacted with the vertebrate and/or the vertebrate sample.

The contact with the PDE inhibitor reduces one or more activity levels in the contacted nematodes as compared to levels of the one or more activities in the non-contacted control *Meliodogyne* or *Heterodera* nematodes.

REFERENCES

Wormbase. WormBase web site, www.wormbase.org, release WS235. 2013.

Bargmann, C. I., Hartwieg, E., and Horvitz, H. R. (1993). Odorant-selective genes and neurons mediate olfaction in *C. elegans*. Cell 74, 515-527.

Barker, K. R., Hussey, R. S., Krusberg, L. R., Bird, G. W., Dunn, R. A., Ferris, H., Ferris, V. R., Freckman, D. W., Gabriel, C. J., Grewal, P. S., Macguidwin, A. E., Riddle, D. L., Roberts, P. A., and Schmitt, D. P. (1994). Plant and soil nematodes: societal impact and focus for the future. J. Nematol. 26, 127-137.

Bender, A. T. and Beavo, J. A. (2006). Cyclic nucleotide phosphodiesterases: molecular regulation to clinical use. Pharmacol. Rev. 58, 488-520.

Brenner, S. (1974). The genetics of *Caenorhabditis elegans*. Genetics 77, 71-94.

Burgin, A. B., Magnusson, O. T., Singh, J., Witte, P., Staker, B. L., Bjornsson, J. M., Thorsteinsdottir, M., Hrafnsdottir, S., Hagen, T., Kiselyov, A. S., Stewart, L. J., and Gurney, M. E. (2010). Design of phosphodiesterase 4D (PDE4D) allosteric modulators for enhancing cognition with improved safety. Nat. Biotechnol. 28, 63-70.

Cahill, K. B., Quade, J. H., Carleton, K. L., and Cote, R. H. (2012). Identification of amino acid residues responsible for the selectivity of tadalafil binding to two closely related phosphodiesterases, PDE5 and PDE6. J. Biol. Chem. 287, 41406-41416.

Carleton, K. L., Spady, T. C., and Cote, R. H. (2005). Rod and cone opsin families differ in spectral tuning domains but not signal transducing domains as judged by saturated evolutionary trace analysis. J. Mol. Evol. 61, 75-89.

Cote, R. H. (2000). Kinetics and regulation of cGMP binding to noncatalytic binding sites on photoreceptor phosphodiesterase. Methods Enzymol. 315, 646-672.

D'Amours, M. R., Granovsky, A. E., Artemyev, N. O., and Cote, R. H. (1999). The potency and mechanism of action of E4021, a PDE5-selective inhibitor, on the photoreceptor phosphodiesterase depends on its state of activation. Mol. Pharmacol. 55, 508-514.

Francis, S. H., Blount, M. A., and Corbin, J. D. (2011). Mammalian cyclic nucleotide phosphodiesterases: molecular mechanisms and physiological functions. Physiol. Rev. 91, 651-690.

Fudali, S. L., Wang, C., and Williamson, V. M. (2013). Ethylene signaling pathway modulates attractiveness of host roots to the root-knot nematode *Meloidogyne hapla*. Mol. Plant Microbe Interact. 26, 75-86.

Handoo, Z. A. Plant-parasitic nematodes. USDA Agricultural Research Service. 1998.

Kano, T., Brockie, P. J., Sassa, T., Fujimoto, H., Kawahara, Y., Iino, Y., Mellem, J. E., Madsen, D. M., Hosono, R., and Maricq, A. V. (2008). Memory in *Caenorhabditis elegans* is mediated by NMDA-type ionotropic glutamate receptors. Curr. Biol. 18, 1010-1015.

L'Etoile, N. D., Coburn, C. M., Eastham, J., Kistler, A., Gallegos, G., and Bargmann, C. I. (2002). The cyclic GMP-dependent protein kinase EGL-4 regulates olfactory adaptation in *C. elegans*. Neuron 36, 1079-1089.

Lichtarge, O. and Sowa, M. E. (2002). Evolutionary predictions of binding surfaces and interactions. Curr. Opin. Struct. Biol. 12, 21-27.

Lin, C. H., Sa, S., Chand, J., and Rankin, C. H. (2013). Dynamic and persistent effects of ethanol exposure on development: an in vivo analysis during and after embryonic ethanol exposure in *Caenorhabditis elegans*. Alcohol Clin. Exp. Res. 37 Suppl 1, E190-E198.

Lugnier, C. (2006). Cyclic nucleotide phosphodiesterase (PDE) superfamily: A new target for the development of specific therapeutic agents. Pharmacol. Ther. 109, 366-398.

Matsuura, T., Oda, T., Hayashi, G., Sugisaki, D., and Ichinose, M. (2010). Enhancement of chemotactic response to sodium acetate in the nematode *Caenorhabditis elegans*. Zoolog. Sci. 27, 629-637.

Nitao, J. K., Meyer, S. L., and Chitwood, D. J. (1999). In-vitro assays of *Meloidogyne incognita* and *Heterodera glycines* for detection of nematode-antagonistic fungal compounds. J. Nematol. 31, 172-183.

O'Halloran, D. M., Hamilton, O. S., Lee, J. I., Gallegos, M., and L'Etoile, N. D. (2012). Changes in cGMP levels affect the localization of EGL-4 in AWC in *Caenorhabditis elegans*. PLoS One 7, e31614.

Ramot, D., Johnson, B. E., Berry, T. L., Jr., Carnell, L., and Goodman, M. B. (2008). The Parallel Worm Tracker: a platform for measuring average speed and drug-induced paralysis in nematodes. PLoS One 3, e2208.

Talavera, M. and Mizukubo, T. (2005). Effects of DL-methionine on hatching and activity of *Meloidogyne incognita* eggs and juveniles. Pest. Manag. Sci. 61, 413-416.

Wang, C., Lower, S., and Williamson, V. M. Application of Pluronic gel to the study of root-knot nematode behavior. J. Nematol. 11[3], 453-464. 2009.

Ward, S. (1973). Chemotaxis by the nematode *Caenorhabditis elegans*: identification of attractants and analysis of the response by use of mutants. Proc. Natl. Acad. Sci. U.S.A. 70, 817-821.

Zhang, X., Feng, Q., and Cote, R. H. (2005). Efficacy and selectivity of phosphodiesterase-targeted drugs in inhibiting photoreceptor phosphodiesterase (PDE6) in retinal photoreceptors. Invest. Ophthalmol. Vis. Sci. 46, 3060-3066.

EQUIVALENTS

Although several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto; the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

All references, patents and patent applications and publications that are cited or referred to in this application are incorporated in their entirety herein by reference.

The invention claimed is:

1. A method of identifying a candidate phytoparasitic nematode phosphodiesterase (PDE) inhibitor compound that disrupts cyclic nucleotide metabolism in a phytoparasitic nematode, the method comprising:
   a) contacting a phytoparasitic nematode test sample with a test compound under conditions suitable for PDE activity;
   b) measuring the level of PDE activity in the test sample;
   c) comparing the measured level of PDE activity in the test sample to a control level of PDE activity, wherein the control comprises a vertebrate sample contacted with the candidate compound under suitable conditions for PDE activity in the vertebrate sample; and
   d) determining whether the contacted test sample has a reduced level of PDE activity relative to the control level of PDE activity, wherein a reduced level of PDE activity in the test sample relative to the control level of PDE activity identifies the test compound as a candidate phytoparasitic nematode PDE inhibitor compound that disrupts cyclic nucleotide metabolism in the phytoparasitic nematode, and wherein the reduced level of PDE activity in the test sample relative to the control sample further identifies the test compound as selectively disrupting cyclic nucleotide metabolism in the phytoparasitic nematode compared to the vertebrate.

2. The method of claim 1, wherein the vertebrate PDE is an ortholog of the phytoparasitic nematode PDE.

3. The method of claim 1, further comprising,
determining one or more amino acid differences between a sequence of a catalytic domain of the phytoparasitic nematode PDE and a sequence of a corresponding catalytic domain of a non-phytoparasitic nematode PDE ortholog or a vertebrate PDE ortholog; and
selecting the test compound based at least in part on the one or more identified differences between the catalytic domain sequences.

4. A method of identifying a candidate phytoparasitic nematode phosphodiesterase (PDE) inhibitor compound that disrupts cyclic nucleotide metabolism in a phytoparasitic nematode, the method comprising:
   a) contacting a phytoparasitic nematode test sample with a test compound under conditions suitable for PDE activity;
   b) measuring the level of PDE activity in the test sample;
   c) comparing the measured level of PDE activity in the test sample to a control level of PDE activity, wherein the control comprises a non-phytoparasitic nematode sample contacted with the test compound under suitable conditions for PDE activity in the non-phytoparasitic nematode sample; and
   d) determining whether the contacted test sample has a reduced level of PDE activity relative to the control level of PDE activity, wherein a reduced level of PDE activity in the test sample relative to the control level of PDE activity identifies the test compound as a candidate phytoparasitic nematode PDE inhibitor compound that disrupts cyclic nucleotide metabolism in the phytoparasitic nematode, and wherein the reduced level of PDE activity in the test sample relative to the control level of PDE activity further identifies the test compound as selectively disrupting cyclic nucleotide metabolism in the phytoparasitic nematode compared to the non- phytoparasitic nematode.

5. The method of claim 4, further comprising,
determining one or more amino acid differences between a sequence of a catalytic domain of the phytoparasitic nematode PDE and a sequence of a corresponding catalytic domain of a non-phytoparasitic nematode PDE ortholog or a vertebrate PDE ortholog; and
selecting the test compound based at least in part on the one or more identified differences between the catalytic domain sequences.

\* \* \* \* \*

SEQUENCE LISTING

```
<160> NUMBER OF SEQ ID NOS: 4

<210> SEQ ID NO 1
<211> LENGTH: 274
<212> TYPE: PRT
<213> ORGANISM: Meloidogyne hapla

<400> SEQUENCE: 1

Asp Ile Pro His Asn Arg Ile His Ala Ala Asp Val Leu His Gly Cys
1               5                   10                  15

Phe Tyr Leu Thr Cys His Ala Val Gln Ala Phe Tyr Leu Met Ala Leu
            20                  25                  30

Phe Ser Ala Ala Ala Met His Asp Tyr Asp His Pro Gly Arg Thr Asn
        35                  40                  45

Ala Phe Leu Val Ala Ser Glu Asp Lys Lys Ala Ile Leu Tyr Asn Asp
    50                  55                  60

Arg Ser Val Leu Glu Asn His His Ala Ala Glu Ser Trp Lys Leu Leu
65                  70                  75                  80

Thr Ser Gln Ser Ser Tyr Asn Phe Ile Glu Ser Leu Asp Ser Ala Glu
                85                  90                  95

Thr Lys Arg Phe Phe Arg Tyr Leu Val Leu Glu Tyr Ile Leu Ala Thr
            100                 105                 110

Asp Leu Lys Gln His Phe Asp Ile Ile Val Gln Phe Asn Glu Arg Ala
        115                 120                 125

Pro Ser Met Asp Leu Ser Asn Glu Ser Asp Arg Met Leu Ile Ser Leu
    130                 135                 140

Met Ile Ile Lys Phe Ala Asp Ile Asn Ser Pro Ala Lys Pro Tyr Ser
145                 150                 155                 160

Leu His Lys Gln Trp Thr Glu Arg Ile Cys Gln Glu Phe Tyr Glu Gln
```

-continued

```
                165                 170                 175
Gly Asp Glu Glu Arg Leu Arg Asn Met Ala Ile Ser Pro Tyr Met Asp
            180                 185                 190

Arg Ser Glu Pro Ala Val Ala Lys Leu Gln Asp Ser Phe Ile Ala His
        195                 200                 205

Ile Val Asn Pro Leu Ala Ile Ala Leu Asn Glu Ala Asn Leu Leu Pro
    210                 215                 220

Ile Leu Pro Gly Leu Pro Glu Ser Gly Leu Arg His Asn His Gln Lys
225                 230                 235                 240

Trp Leu Asn Gln Ile Glu Phe Asp Gln Lys His Cys Arg Glu Ser Glu
                245                 250                 255

Glu Asp Glu Lys Arg Gly Asn Ala Leu Gly Asn Asn Lys Thr Asn Ile
            260                 265                 270

Ser Arg

<210> SEQ ID NO 2
<211> LENGTH: 318
<212> TYPE: PRT
<213> ORGANISM: Heterodera glycines

<400> SEQUENCE: 2

Asp Arg Ala Glu Leu Glu Arg Asp Pro Ala Leu Gly Gln Ile Gln Glu
1               5                   10                  15

Trp Ser Phe Pro Ile Phe Arg Leu Ala Glu Lys His Lys Arg Thr Val
                20                  25                  30

Ser Arg Leu Thr Tyr Ala Ile Phe Lys Glu Ala Asp Leu Phe Arg Thr
            35                  40                  45

Phe Lys Ile Ser Tyr Thr Lys Phe Phe Asn Phe Phe His Ala Leu Glu
        50                  55                  60

Ser Gly Tyr Trp Asp Ile Pro Tyr His Asn Arg Ile His Ala Ala Asp
65                  70                  75                  80

Val Leu His Gly Thr Tyr Tyr Leu Thr Cys His Pro Val His Ala Phe
                85                  90                  95

Cys Arg Gln Met Pro Phe Asp Phe Gly Asn Tyr Ile Glu Ser Ile Leu
            100                 105                 110

Lys Asn Ser Phe Val Pro Leu Met Ala Leu Tyr Thr Ala Ala Ala Met
        115                 120                 125

His Asp Tyr Asp His Pro Gly Arg Thr Asn Ala Phe Leu Val Ala Ser
    130                 135                 140

Glu Asp Arg Lys Ala Ile Leu Tyr Asn Asp Arg Ser Val Leu Glu Asn
145                 150                 155                 160

His His Ala Ala Glu Ser Trp Arg Leu Leu Asn Ser His Ala Gln Phe
                165                 170                 175

Gln Phe Ile Glu Asn Leu Asp Ser Ala Glu Thr Lys Arg Phe Arg Tyr
            180                 185                 190

Leu Val Leu Glu Tyr Ile Leu Ala Thr Asp Leu Lys Gln His Phe Asp
        195                 200                 205

Ile Ile Met Gln Phe Asn Glu Arg Val Pro Asp Met Asp Leu Asn Ser
    210                 215                 220

Glu Ser Asp Arg Val Leu Ile Ser Leu Met Leu Ile Asn Leu Ile Cys
225                 230                 235                 240

Gln Glu Phe Tyr Glu Gln Gly Asp Asp Glu Lys Arg Arg Lys Met Pro
                245                 250                 255

Val Ser Pro Tyr Met Asp Arg Asn Glu Pro Ala Val Ala Lys Leu Gln
```

```
            260                 265                 270

Asp Ser Phe Ile Ala His Ile Val Asn Pro Leu Ala Ile Ala Leu Asn
        275                 280                 285

Glu Ala Gly Leu Phe Pro Val Leu Pro Gly Leu Pro Glu Ser Glu Leu
    290                 295                 300

Ile Ile Asn Leu Lys His Asn His Gln Lys Trp Leu His Gln
305                 310                 315

<210> SEQ ID NO 3
<211> LENGTH: 279
<212> TYPE: PRT
<213> ORGANISM: Caenorhabditis elegans

<400> SEQUENCE: 3

Ser Ser Ile Met Ser Gln Leu Ser Thr Leu Glu Leu Met Ala Leu Phe
1               5                   10                  15

Thr Ala Ala Met His Asp Tyr Asp His Pro Gly Arg Thr Asn Ala
            20                  25                  30

Phe Leu Val Gln Val Glu Asp Lys Ala Ile Leu Tyr Asn Asp Arg
        35                  40                  45

Ser Val Leu Glu Asn His His Ala Ala Glu Ser Trp Lys Leu Leu Asn
    50                  55                  60

Lys Pro Glu Asn His Phe Ile Glu Asn Leu Asp Pro Ala Glu Met Lys
65                  70                  75                  80

Arg Phe Arg Tyr Leu Val Leu Glu Tyr Ile Leu Ala Thr Asp Leu Lys
                85                  90                  95

Gln His Phe Glu Ile Ile Met Thr Phe Thr Arg Leu Thr Glu Ile
            100                 105                 110

Asp Val Gln Val Glu Thr Asp Arg Leu Leu Ile Gly Lys Leu Leu Ile
        115                 120                 125

Lys Met Ala Asp Ile Asn Ser Pro Thr Lys Pro Tyr Gly Leu His Arg
130                 135                 140

Gln Trp Thr Asp Arg Ile Cys Glu Glu Phe Tyr Glu Gln Gly Asp Asp
145                 150                 155                 160

Glu Arg Arg Arg Gly Leu Pro Ile Thr Pro Tyr Met Asp Arg Gly Asp
                165                 170                 175

Ala Gln Val Ala Lys Leu Gln Asp Ser Phe Ile Ala His Val Val Ser
            180                 185                 190

Pro Leu Ala Thr Ala Met Asn Glu Cys Gly Leu Leu Pro Ile Leu Pro
        195                 200                 205

Gly Leu Asp Thr Ser Glu Leu Ile Ile Asn Met Glu His Asn His Arg
    210                 215                 220

Lys Trp Lys Glu Gln Ile Glu Leu Glu Asn Gly Gly Ser Tyr Glu Ala
225                 230                 235                 240

Gln Ile Thr Cys Asn Gly Gly Thr Ala Val Asn Gly Val Ile Glu Glu
                245                 250                 255

Glu Ser Ala Ser Thr Ser Asp Ser Pro Asp Pro Arg Arg Asp Ser Pro
            260                 265                 270

Leu Asp Ser Asp Leu Ser Gln
        275

<210> SEQ ID NO 4
<211> LENGTH: 421
<212> TYPE: PRT
<213> ORGANISM: Homo sapiens
```

```
<400> SEQUENCE: 4

Asp Met Gly Leu Phe Glu Ala Phe Lys Ile Pro Ile Arg Glu Phe Met
1               5                   10                  15

Asn Tyr Phe His Ala Leu Glu Ile Gly Tyr Arg Asp Ile Pro Tyr His
            20                  25                  30

Asn Arg Ile His Ala Thr Asp Val Leu His Ala Val Trp Tyr Leu Thr
        35                  40                  45

Thr Gln Pro Ile Pro Gly Leu Ser Thr Val Ile Asn Asp His Gly Ser
    50                  55                  60

Thr Ser Asp Ser Asp Ser Asp Ser Gly Phe Thr His Gly His Met Gly
65                  70                  75                  80

Tyr Val Phe Ser Lys Thr Tyr Asn Val Thr Asp Asp Lys Tyr Gly Cys
                85                  90                  95

Leu Ser Gly Asn Ile Pro Ala Leu Glu Leu Met Ala Leu Tyr Val Ala
            100                 105                 110

Ala Ala Met His Asp Tyr Asp His Pro Gly Arg Thr Asn Ala Phe Leu
        115                 120                 125

Val Ala Thr Ser Ala Pro Gln Ala Val Leu Tyr Asn Asp Arg Ser Val
    130                 135                 140

Leu Glu Asn His His Ala Ala Ala Ala Trp Asn Leu Phe Met Ser Arg
145                 150                 155                 160

Pro Glu Tyr Asn Phe Leu Ile Asn Leu Asp His Val Glu Phe Lys His
                165                 170                 175

Phe Arg Phe Leu Val Ile Glu Ala Ile Leu Ala Thr Asp Leu Lys Lys
            180                 185                 190

His Phe Asp Phe Val Ala Lys Phe Asn Gly Lys Val Asn Asp Asp Val
        195                 200                 205

Gly Ile Asp Trp Thr Asn Glu Asn Asp Arg Leu Leu Val Cys Gln Met
    210                 215                 220

Cys Ile Lys Leu Ala Asp Ile Asn Gly Pro Ala Lys Cys Lys Glu Leu
225                 230                 235                 240

His Leu Gln Trp Thr Asp Gly Ile Val Asn Glu Phe Tyr Glu Gln Gly
                245                 250                 255

Asp Glu Glu Ala Ser Leu Gly Leu Pro Ile Ser Pro Phe Met Asp Arg
            260                 265                 270

Ser Ala Pro Gln Leu Ala Asn Leu Gln Glu Ser Phe Ile Ser His Ile
        275                 280                 285

Val Gly Pro Leu Cys Asn Ser Tyr Asp Ser Ala Gly Leu Met Pro Gly
    290                 295                 300

Lys Trp Val Glu Asp Ser Asp Glu Ser Gly Asp Thr Asp Asp Pro Glu
305                 310                 315                 320

Glu Glu Glu Glu Glu Ala Pro Ala Pro Asn Glu Glu Glu Thr Cys Glu
                325                 330                 335

Asn Asn Glu Ser Pro Lys Lys Lys Thr Phe Lys Arg Arg Lys Ile Tyr
            340                 345                 350

Cys Gln Ile Thr Gln His Leu Leu Gln Asn His Lys Met Trp Lys Lys
        355                 360                 365

Val Ile Glu Glu Glu Gln Arg Leu Ala Gly Ile Glu Asn Gln Ser Leu
    370                 375                 380
```

```
Asp Gln Thr Pro Gln Ser His Ser Ser Glu Gln Ile Gln Ala Ile Lys
385                 390                 395                 400

Glu Glu Glu Glu Glu Lys Gly Lys Pro Arg Gly Glu Glu Ile Pro Thr
                405                 410                 415

Gln Lys Pro Asp Gln
            420
```